(12) United States Patent
Meyer et al.

(10) Patent No.: US 12,014,835 B2
(45) Date of Patent: Jun. 18, 2024

(54) METHODS FOR EVALUATING THERAPEUTIC BENEFIT OF COMBINATION THERAPIES

(71) Applicants: Vanderbilt University, Nashville, TN (US); DUET Biosystems, Inc., Nashville, TN (US)

(72) Inventors: Christian T. Meyer, Nashville, TN (US); Vito Quaranta, Nashville, TN (US); Leonard A. Harris, Nashville, TN (US); Buddhi Bishal Paudel, Nashville, TN (US); David J. Wooten, Nashville, TN (US); Laurent Audoly, Brookline, MA (US)

(73) Assignees: Vanderbilt University, Nashville, TN (US); Duet BioSystems Inc., Nashville, TN (US)

( * ) Notice: Subject to any disclaimer, the term of this patent is extended or adjusted under 35 U.S.C. 154(b) by 466 days.

(21) Appl. No.: 17/180,280

(22) Filed: Feb. 19, 2021

(65) Prior Publication Data

US 2021/0358642 A1  Nov. 18, 2021

Related U.S. Application Data

(60) Provisional application No. 62/978,530, filed on Feb. 19, 2020.

(51) Int. Cl.
*G16H 70/20* (2018.01)
*G16C 20/30* (2019.01)

(52) U.S. Cl.
CPC ............. *G16H 70/20* (2018.01); *G16C 20/30* (2019.02)

(58) Field of Classification Search
CPC ........ G16H 70/20; G16H 20/10; G16H 50/20; G16C 20/30
See application file for complete search history.

(56) References Cited

U.S. PATENT DOCUMENTS

| | | | |
|---|---|---|---|
| 6,214,379 B1 * | 4/2001 | Hermelin | A61K 31/277 424/463 |
| 9,381,193 B2 | 7/2016 | Moley et al. | |
| 10,028,971 B2 * | 7/2018 | Bird | A61K 31/4166 |
| 10,839,950 B2 * | 11/2020 | Vaughan | G16H 50/20 |
| 2003/0135128 A1 * | 7/2003 | Suffin | A61B 5/411 600/300 |

(Continued)

FOREIGN PATENT DOCUMENTS

| | | | | |
|---|---|---|---|---|
| CN | 1697831 A | * | 11/2005 | ........... C07D 251/18 |
| WO | WO2003012072 A2 | | 2/2003 | |

(Continued)

OTHER PUBLICATIONS

Nitulescu et al., "Akt inhibitors in cancer treatment: The long journey from drug discovery to clinical use", Int. J. Oncol., vol. 48, No. 3, 2016, pp. 869-885.

(Continued)

*Primary Examiner* — Tung S Lau
(74) *Attorney, Agent, or Firm* — Michael Best & Friedrich LLP

(57) ABSTRACT

The invention provides methods for evaluating the therapeutic benefit of a combination therapy useful for treating a medical disorder, such as cancer.

20 Claims, 19 Drawing Sheets
(16 of 19 Drawing Sheet(s) Filed in Color)

(56) References Cited

U.S. PATENT DOCUMENTS

| | | |
|---|---|---|
| 2004/0018987 A1 | 1/2004 | Hoffman et al. |
| 2006/0128636 A1 | 6/2006 | Yamazaki et al. |
| 2006/0233808 A1 | 10/2006 | Deperthes et al. |
| 2007/0037883 A1 | 2/2007 | Dusting et al. |
| 2009/0093538 A1 | 4/2009 | Bertin et al. |
| 2009/0142413 A1* | 6/2009 | Allen ............... A61K 51/1255 514/56 |
| 2013/0172552 A1 | 7/2013 | Hernandez et al. |
| 2014/0187566 A1 | 7/2014 | Dumble et al. |
| 2016/0287595 A1 | 10/2016 | Liu et al. |
| 2017/0157132 A1 | 6/2017 | Wu et al. |
| 2019/0043610 A1* | 2/2019 | Vaughan ............... G16H 50/70 |
| 2019/0247427 A1 | 8/2019 | Wilson et al. |

FOREIGN PATENT DOCUMENTS

| | | |
|---|---|---|
| WO | WO2003070912 A2 | 8/2003 |
| WO | WO2006083051 A1 | 8/2006 |
| WO | WO2008005983 A2 | 1/2008 |
| WO | WO2008054599 A2 | 5/2008 |
| WO | WO2008098104 A1 | 8/2008 |
| WO | WO2008127656 A1 | 10/2008 |
| WO | WO2009009523 A2 | 1/2009 |
| WO | WO2009044392 A2 | 7/2009 |
| WO | WO2009158587 A1 | 12/2009 |
| WO | WO2010065711 A1 | 6/2010 |
| WO | WO2010104851 A1 | 9/2010 |
| WO | WO2011050210 A1 | 4/2011 |
| WO | WO2012007632 A1 | 1/2012 |
| WO | WO2012171506 A1 | 12/2012 |
| WO | WO2013001372 A2 | 1/2013 |
| WO | WO2014055996 A2 | 4/2014 |
| WO | WO2014134391 A1 | 9/2014 |
| WO | WO2015054317 A1 | 4/2015 |
| WO | WO2015121210 A1 | 8/2015 |
| WO | WO2016106331 A1 | 6/2016 |
| WO | WO2016179576 A1 | 11/2016 |
| WO | WO2017146795 A1 | 8/2017 |
| WO | WO2018093856 A1 | 5/2018 |
| WO | WO2018204278 A1 | 11/2018 |
| WO | WO2019023315 A2 | 1/2019 |
| WO | WO2019194598 A1 | 10/2019 |
| WO | WO2019222553 A1 | 11/2019 |

OTHER PUBLICATIONS

Elliott et al., "Inhibition Glutathione Reductase by Flavonoids", Biochemical Pharmacology, vol. 44, Issue 8, 1992, pp. 1603-1608.

Hamilton et al., "Novel Steroid Inhibitors of Glucose 6-Phosphate Dehydrogenase", J. Med. Chem., vol. 55, No. 9, 2012, pp. 4431-4445.

Thysiadis et al., "Design and synthesis of gallocyanine inhibitors of DKK1/LRP6 interactions for treatment of Alzheimer's disease", Bioorganic Chem., vol. 80, 2018, pp. 230-244.

Jung et al., "Development of a Novel Class of Mitochondrial Ubiquinol-Cytochrome c Reductase Binding Protein (UQCRB) Modulators as Promising Antiangiogenic Leads", J. Med. Chem., vol. 57, No. 19, 2014, pp. 7990-7998.

Harris et al., "An unbiased metric of antiproliferative drug effect in vitro", Nature Methods, vol. 13, 2016, pp. 497-500.

Berg et al., "Deviance Information Criterion for Comparing Stochastic Volatility Models".

Bliss, "The Toxicity of Poisons Applied Jointly", Annals of Applied Biology, vol. 26, No. 3, 1939, pp. 585-616.

Chou et al., "Analysis of combined drug effects: a new look at a very old problem", Trends in Pharmacological Sciences, 1983, vol. 4, pp. 450-454.

Chou et al., "Quantitative analysis of dose-effect relationships: the combined effects of multiple drugs or enzyme inhibitors", Advances in enzyme regulation, 1984, vol. 22, pp. 27-55.

Eroglu et al., "Combination therapy with BRAF and MEK inhibitors for melanoma: latest evidence and place in therapy", Therapeutic advances in medical oncology, SAGE Publications, 2016, vol. 8, No. 1, pp. 48-56.

Foucquier et al., "Analysis of drug combinations: current methodological landscape", Pharmacology research & perspectives, 2015, vol. 3, No. 3, p. e00149.

Gong et al., "Compound Libraries: Recent Advances and Their Applications in Drug Discovery", Current Drug Discovery Technologies, 2017, vol. 14, No. 4, pp. 216-228.

Greco et al., "Consensus on Concepts and Terminology for Combined-action Assessment: The Saariselka Agreement", ACES, 1992, vol. 4, No. 3, pp. 65-69.

Greco et al., "The search for synergy: a critical review from a response surface perspective", Pharmacological reviews, 1995, vol. 47, No. 2, pp. 331-385.

Hanahan et al., "Hallmarks of cancer: the next generation", 2011, Cell. Elsevier, vol. 144, No. 5, pp. 646-674.

Haq et al., "Oncogenic BRAF regulates oxidative metabolism via PGC1α and MITF", Cancer Cell., 2013, vol. 23, No. 3, pp. 302-315.

Hardeman et al., "Dependence on Glycolysis Sensitizes BRAF-mutated Melanomas for Increased Response to Targeted BRAF Inhibition", Scientific Reports, 2017, vol. 7, p. 42604.

He et al., "Combination therapeutics in complex diseases", Journal of Cellular and Molecular Medicine, 2016, vol. 20, No. 12, pp. 2231-2240.

Hunter, "Matplotlib: A 2D Graphics Environment", Computing in Science and Engineering, 2007, vol. 9, No. 3, pp. 90-95.

Inglese et al., "High-throughput screening assays for the identification of chemical probes", Nature Chemical Biology, 2007, vol. 3, No. 8, pp. 466-479.

Janzen, "Screening Technologies for Small Molecule Discovery: The State of the Art", Chemistry & Biology, 2014, vol. 21, No. 9, pp. 1162-1170.

Jaquet et al., "NADPH oxidase (NOX) isoforms are inhibited by celastrol with a dual mode of action", British Journal of Pharmacology, 2011, vol. 164, No. 2b, pp. 507-520.

LeBleu et al. "PGC-1α mediates mitochondrial biogenesis and oxidative phosphorylation in cancer cells to promote metastasis", Nature Cell Biology, 2014, vol. 16, No. 10, pp. 992-1003.

Long et al., "Combined BRAF and MEK Inhibition versus BRAF Inhibition Alone in Melanoma", New England Journal of Medicine, 2014, vol. 371, No. 20, pp. 1877-1888.

Lu et al., "Novel Role of NOX in Supporting Aerobic Glycolysis in Cancer Cells with Mitochondrial Dysfunction and as a Potential Target for Cancer Therapy", PLoS Biology, 2012, vol. 10, No. 5, p. e1001326.

McKinney, "'Data Structures for Statistical Computing in Python", 2010, pp. 51-56.

Meletiadis et al., "Defining fractional inhibitory concentration index cutoffs for additive interactions based on self-drug additive combinations, Monte Carlo simulation analysis, and in vitro-in vivo correlation data for antifungal drug combinations against Aspergillus fumigatus", Antimicrobial Agents and Chemotherapy ASM, 2010, vol. 54, No. 2, pp. 602-609.

Mitchell, "What is complex about complex disorders?", Genome Biology BioMed Central, 2012, vol. 13, No. 1, p. 237.

Mott et al., "High-throughput matrix screening identifies synergistic and antagonistic antimalarial drug combinations", Scientific Reports, 2015, vol. 5, No. 1, p. 13891.

Parmenter et al., "Response of BRAF-mutant melanoma to BRAF inhibition is mediated by a network of transcriptional regulators of glycolysis", Cancer Discovery, 2014, vol. 4, No. 4, pp. 423-433.

Paudel et al., 'A Nonquiescent 'Idling' Population State in Drug-Treated, BRAF-Mutated Melanoma', Biophysical Journal, 2018, vol. 114, No. 6, pp. 1499-1511.

Quaranta et al., "Trait Variability of Cancer Cells Quantified by High-Content Automated Microscopy of Single Cells", Methods in Enzymology, 2009, pp. 23-57.

Rizos et al., "BRAF Inhibitor Resistance Mechanisms in Metastatic Melanoma: Spectrum and Clinical Impact", Clinical Cancer Research, 2014, vol. 20. No. 7, pp. 1965-1977.

(56) References Cited

OTHER PUBLICATIONS

Schiffmann et al., "'Epigenetic therapy approaches in non-small cell lung cancer: Update and perspectives", Epigenetics, 2016, vol. 11, No. 12, pp. 858-870.
Schindler, "Theory of synergistic effects: Hill-type response surfaces as "null-interaction" models for mixtures", Theoretical Biology and Medical Modelling, 2017, vol. 14, No. 1, p. 15.
Sharma et al., "A chromatin-mediated reversible drug-tolerant state in cancer cell subpopulations", Cell, 2010, vol. 141, No. 1, pp. 69-80.
Shaw et al., "Ceritinib in ALK -Rearranged Non-Small-Cell Lung Cancer", New England Journal of Medicine, 2014, vol. 370, No. 13, pp. 1189-1197.
Shimoyama et al., "Cadherin dysfunction in a human cancer cell line: possible involvement of loss of alpha-catenin expression in reduced cell-cell adhesiveness", Cancer Research, 1992, vol. 52, No. 20, pp. 5770-5774.
Smith et al., "Inhibiting Drivers of Non-mutational Drug Tolerance Is a Salvage Strategy for Targeted Melanoma Therapy", Cancer Cell, 2016, vol. 29, pp. 270-284.
Soria et al., "Osimertinib in Untreated EGFR-Mutated Advanced Non-Small-Cell Lung Cancer", New England Journal of Medicine, 2018, vol. 378, No. 2, pp. 113-125.
Subramanian et al., "A Next Generation Connectivity Map: L1000 Platform and the First 1,000,000 Profiles", Cell. Elsevier, 2017, vol. 171, No. 6, pp. 1437-1452.
Tallarida, "Quantitative methods for assessing drug synergism", Genes & Cancer Impact Journals, 2011, vol. 2, No. 11, pp. 1003-1008.
Tang et al., "Erlotinib Resistance in Lung Cancer: Current Progress and Future Perspectives", Frontiers in Pharmacology, vol. 4, Article 15, 9 pages.
Tange, "GNU Parallel: The Command-Line Power Tool", USENIX, 2011, vol. 36, No. 1, pp. 42-47.
Twarog et al., "BRAID: A Unifying Paradigm for the Analysis of Combined Drug Action", Scientific Reports, 2016, vol. 6, No. 1, p. 25523.
Tyson et al., "Fractional proliferation: a method to deconvolve cell population dynamics from single-cell data", Nature Methods, 2012, vol. 9, No. 9, pp. 923-928.
Van der Veeken et al., "Crosstalk between epidermal growth factor receptor- and insulin-like growth factor-1 receptor signaling: implications for cancer therapy", Current Cancer Drug Targets, 2009, vol. 9, No. 6, pp. 748-760.
Van der Walt et al., "scikit-image: image processing in Python", PeerJ, 2, p. e453.
Witta et al., "Restoring E-Cadherin Expression Increases Sensitivity to Epidermal Growth Factor Receptor Inhibitors in Lung Cancer Cell Lines", Cancer Research, 2006, vol. 66, No. 2, pp. 944-950.
Witta et al., "Randomized Phase II Trial of Erlotinib With and Without Entinostat in Patients With Advanced Non-Small-Cell Lung Cancer Who Progressed on Prior Chemotherapy", Journal of Clinical Oncology, 2012, vol. 30, No. 18, pp. 2248-2255.
Yadav et al., "Searching for Drug Synergy in Complex Dose-Response Landscapes Using an Interaction Potency Model", Computational and Structural Biotechnology, 2015, vol. 13, pp. 504-513.
Zimmer et al., "Prediction of multidimensional drug dose responses based on measurements of drug pairs", PNAS, 2016, vol. 113, No. 37, pp. 10442-10447.
Chou et al., "Drug Combination Studies and their Synergy Quantification Using the Chou-Talalay Method", Cancer Research, 2010, vol. 70, No. 2, pp. 440-446.
Ettinger et al., "Non-Small Cell Lung Cancer, Version 5.2017, NCCN Clinical Practical Guidelines in Oncology", Journal of the National Comprehensive Cancer Network, 2017, vol. 15, No. 4, pp. 504-535.
Fallahi-Sichani et al., "Metrics other than potency reveal systematic variation in responses to cancer drugs", Nature Chemical Biology, 2013, vol. 9, No. 11, pp. 708-714.
Hafner et al., "Growth rate inhibition metrics correct for confounders in measuring sensitivity to cancer drugs", Nature Methods, 2016, vol. 13, No. 6, pp. 521-527.
Kim et al., "HISAT: a fast spliced aligner with low memory requirements", Nature Methods, 2015, vol. 12, No. 4, pp. 357-360.
Liao et al., "featureCounts: an efficient general purpose program for assigning sequence reads to genomic features", Bioinformatics, 2014, vol. 30, No. 7, pp. 923-930.
Love et al., "Moderated estimation of fold change and dispersion for RNA-seq data with DESeq2", Genome Biology, 2014, vol. 15, No. 12, pp. 550.
Mokhtari et al., "Combination therapy in combating cancer", Oncotarget, 2015, vol. 8, No. 23, pp. 38022-38043.
Siren et al., "Indexing Graphs for Path Queries with Applications in Genome Research", IEEE Transactions on Computational Biology and Bioinformatics, 2014, vol. 11, No. 2, pp. 375-388.
Vazquez et al., "PGC1α Expression Defines a Subset of Human Melanoma Tumors with Increased Mitochondrial Capactiy and Resistance to Oxidative Stress", Cancer Cell, 2013, vol. 23, No. 3, pp. 287-301.
Yang et al., "Genomics of Drug Sensitivity in Cancer (GDSC): a resource for therapeutic biomarker discovery in cancer cells", Nucleic Acids Research, 2013, vol. 41, pp. 955-961.
Yap et al., "Development of Therapeutic Combinations Targeting Major Cancer Signaling Pathways", Journal of Clinical Oncology, 2013, vol. 31, No. 12, pp. 1592-1605.
Wooten et al., "Quantifying drug combination synergy along axes of potency and efficacy", Oral Presentation Abstracts, Systems Approach to Cancer Biology Conference, 2018, 21 pages, pp. 15-16.
Wooten et al., "Quantifying drug combination synergy along axes of potency and efficacy", Poster Presentation, publicly presented before Feb. 2020 (1 page).
Wooten et al., "2D Dose-response surfaces given by generalized 2D Hill equation", Supplemental dissertation defense information, 2018, 4 pages.
International Search Report and Written Opinion for Application No. PCT/US2021/018822 dated Jun. 21, 2021 (17 pages).
International Preliminary Report on Patentability for Application No. PCT/US2021/018822 dated Aug. 23, 2022 (8 pages).
Jones et al., "SciPy: Open Source Scientific Tools for Python", available at: <http://www.scipy.org/>, Accessed: Mar. 20, 2018 (3 pages).

\* cited by examiner

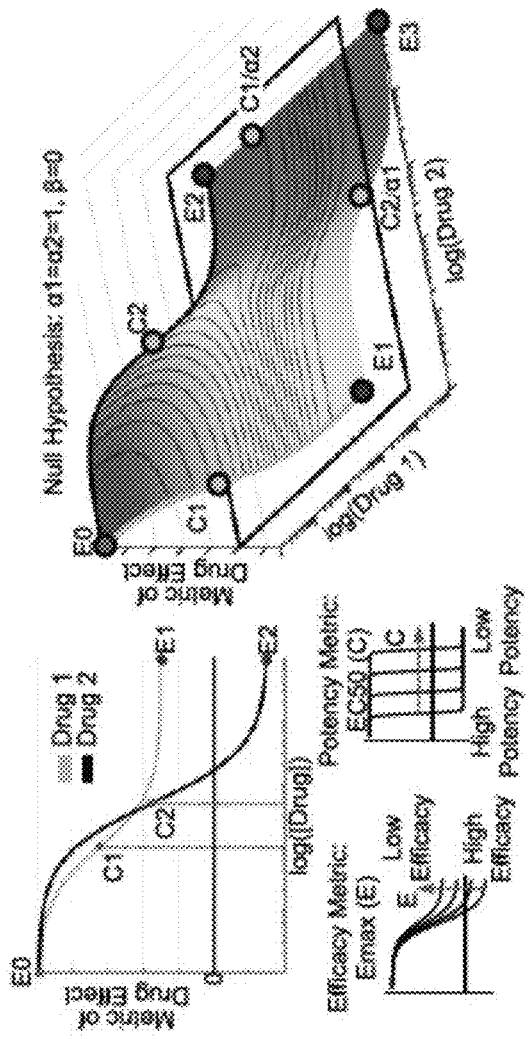
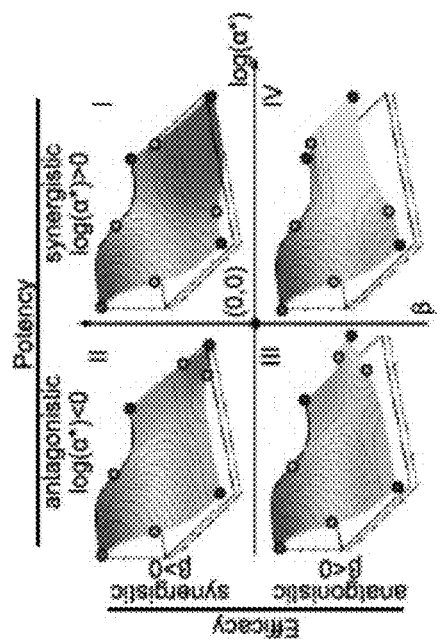
Figure 1A
Figure 1B
Figure 1C

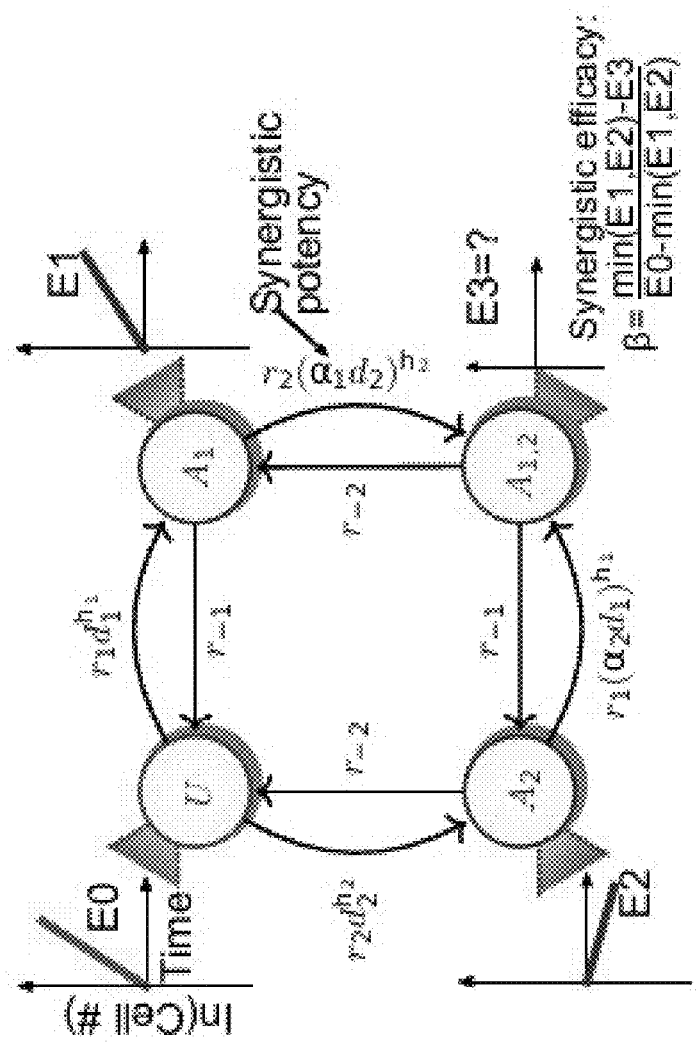
Figure 1-S1B

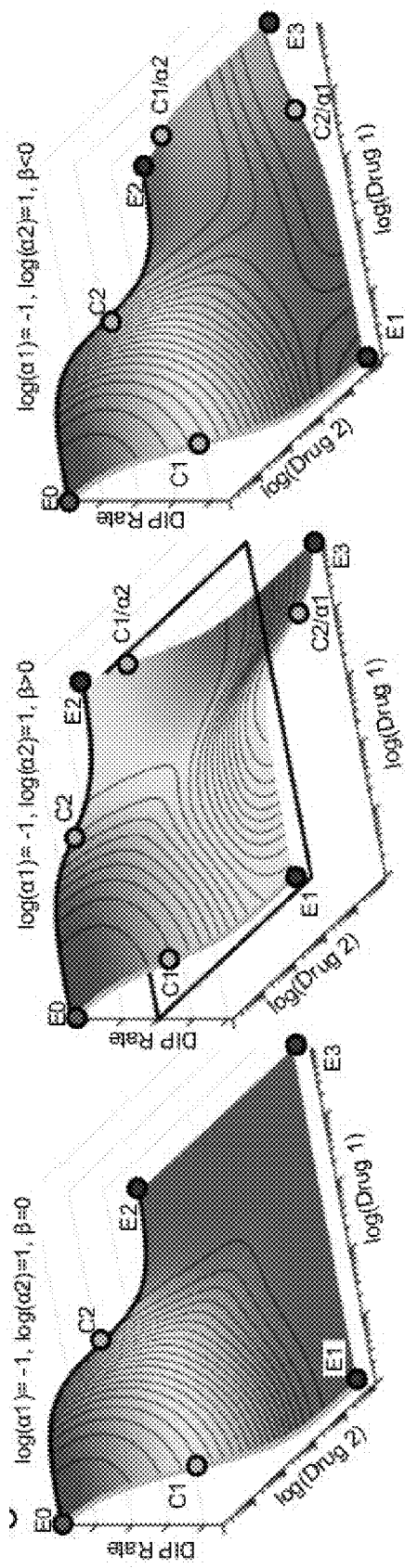
Figure 1-S1C

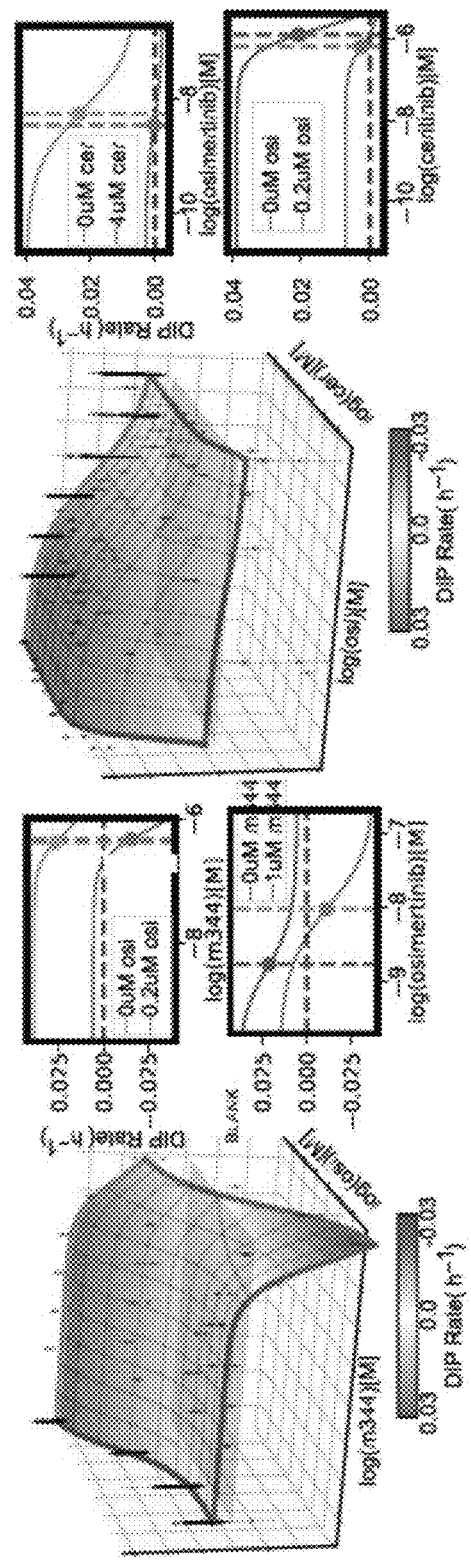

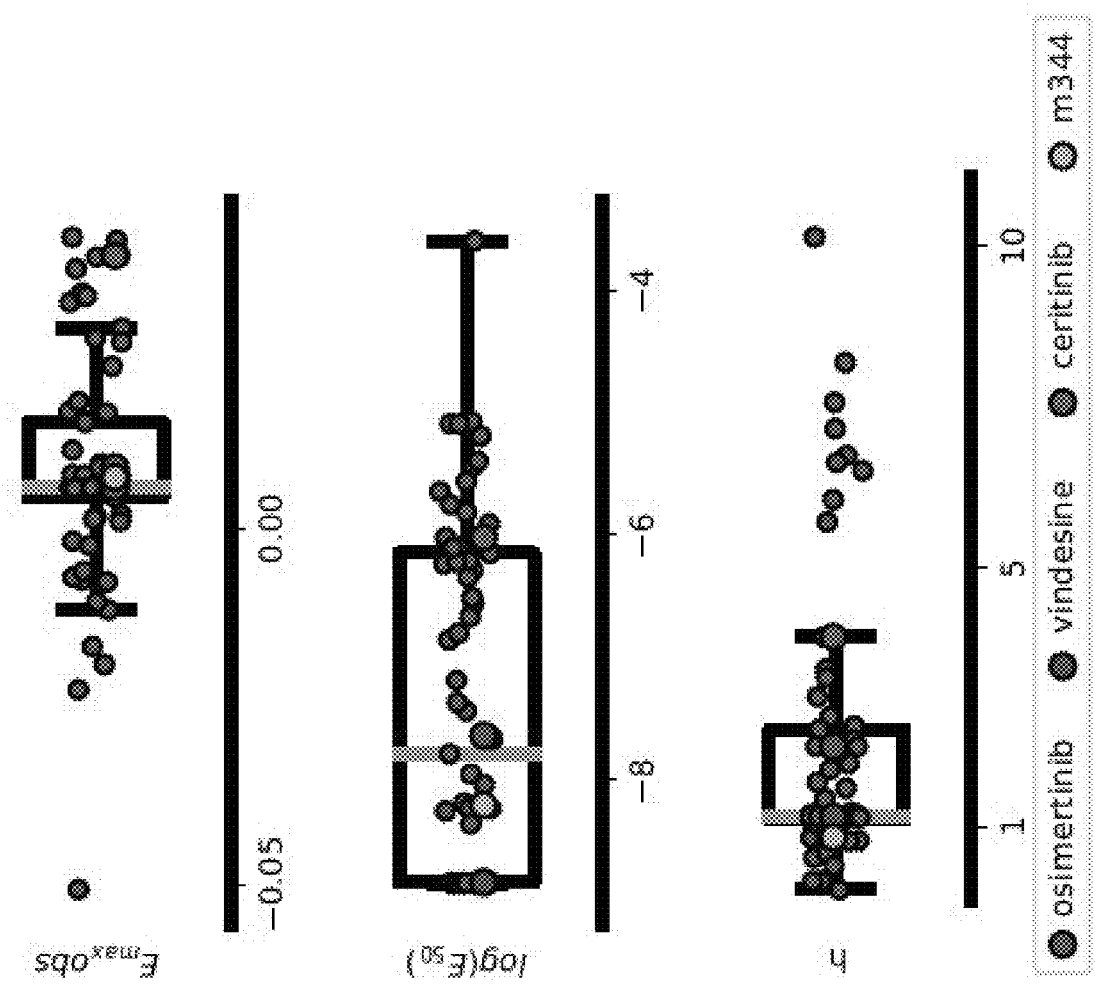
Figure 3-S4A

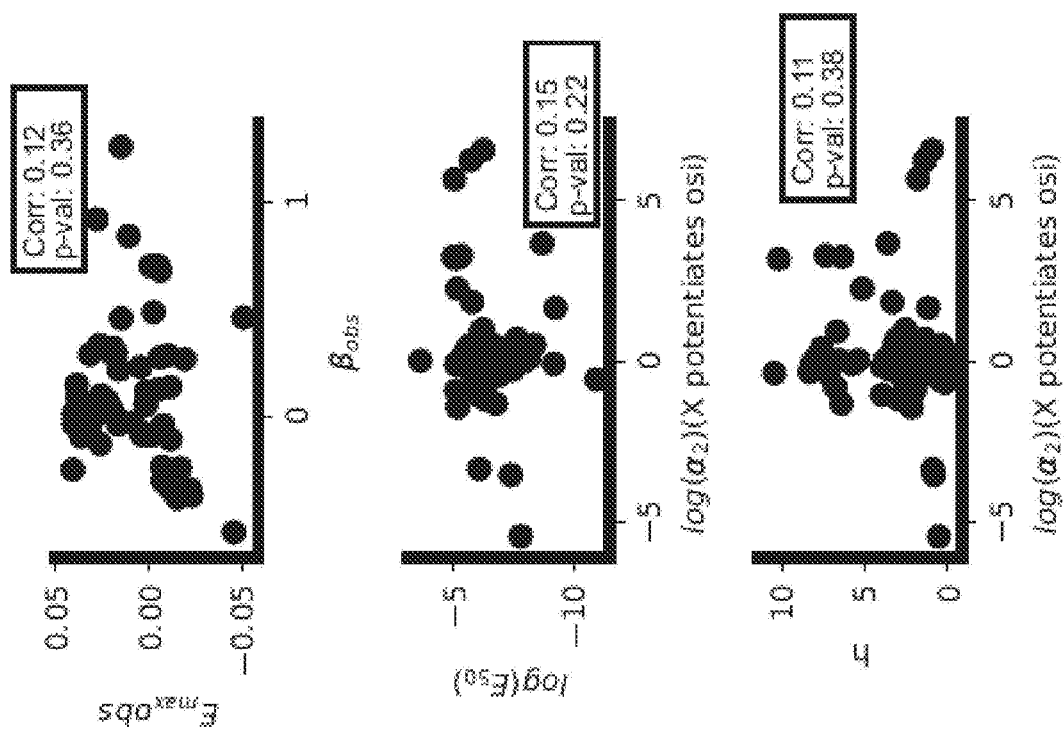
Figure 3-S4B

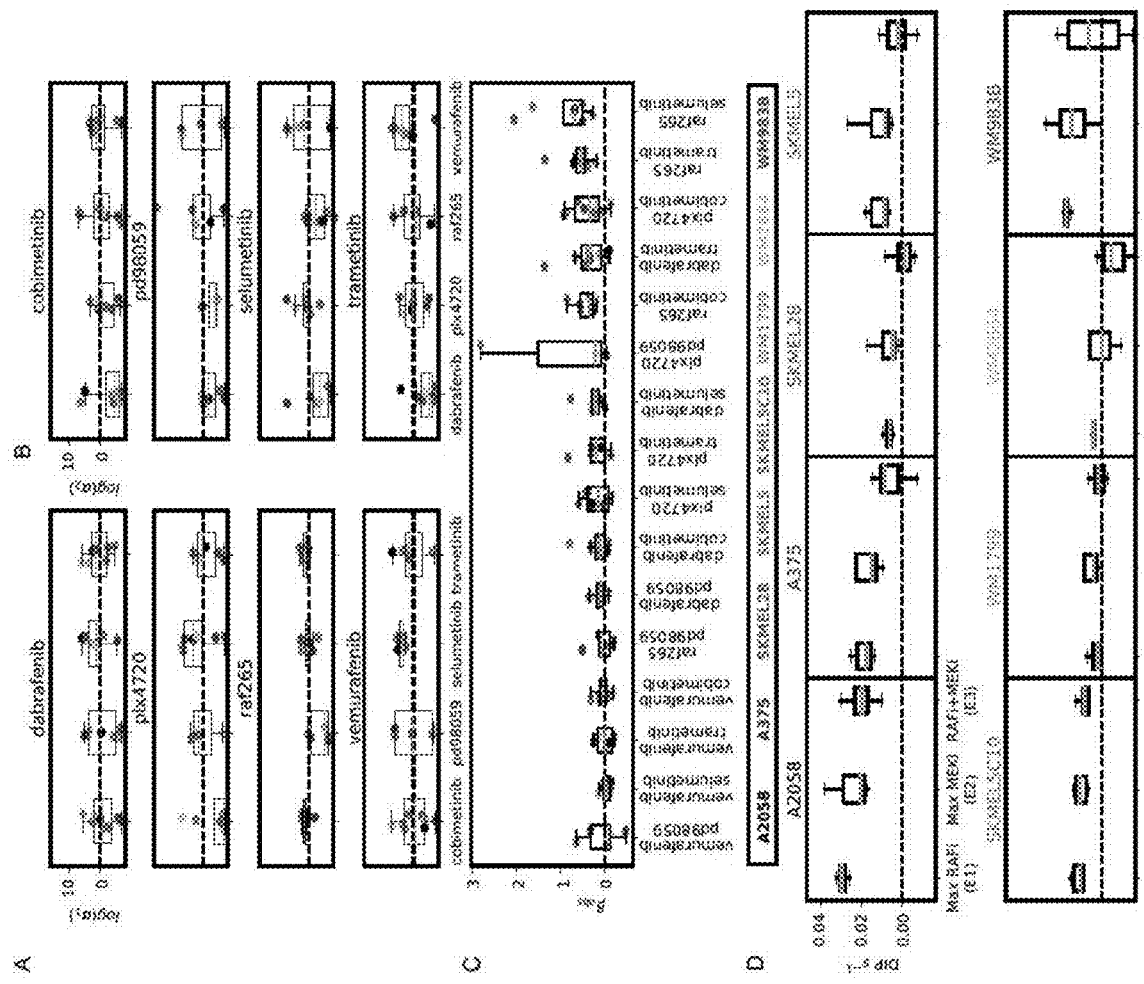
Figure 3-S5

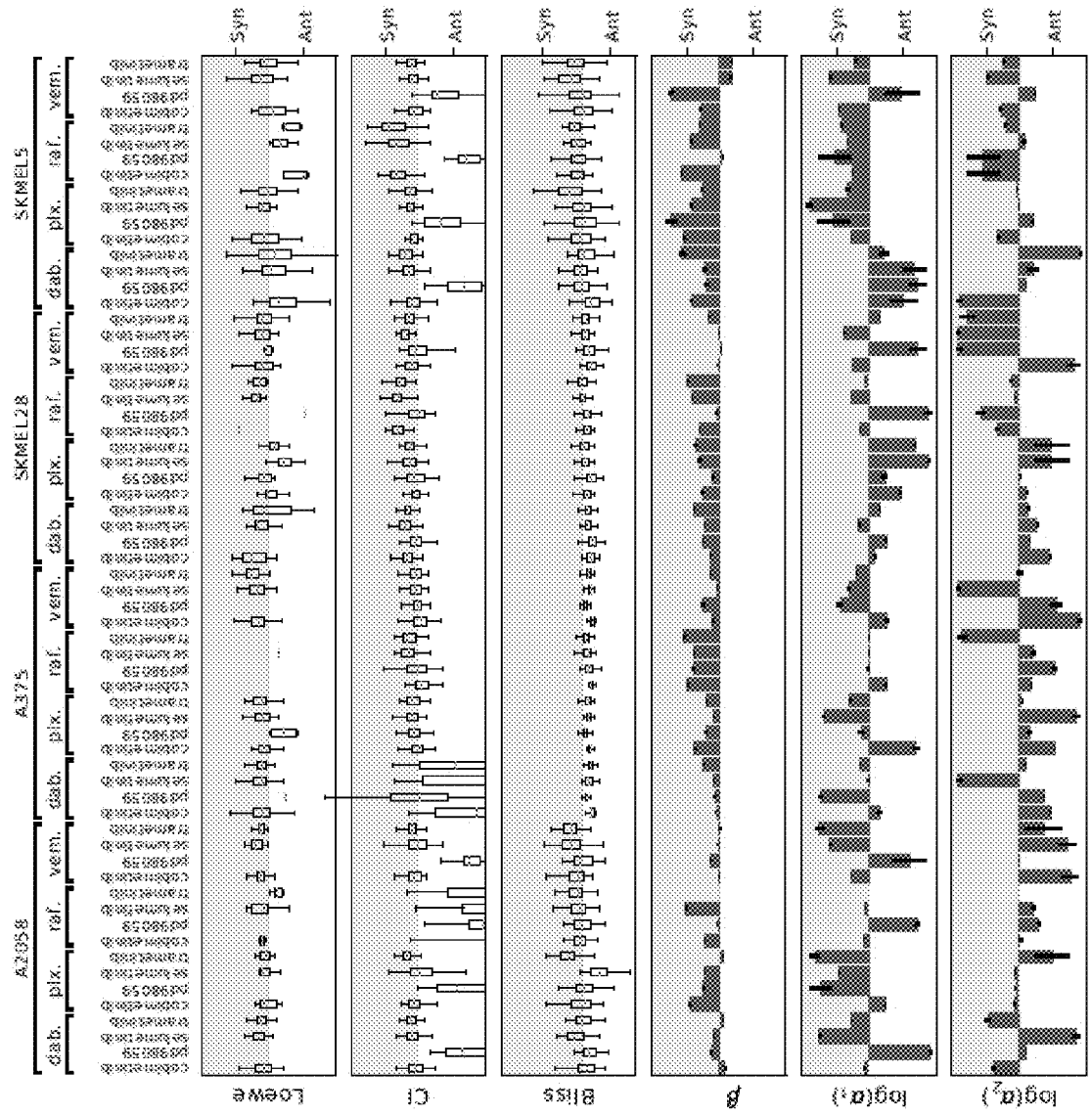
Figure 3-S6A

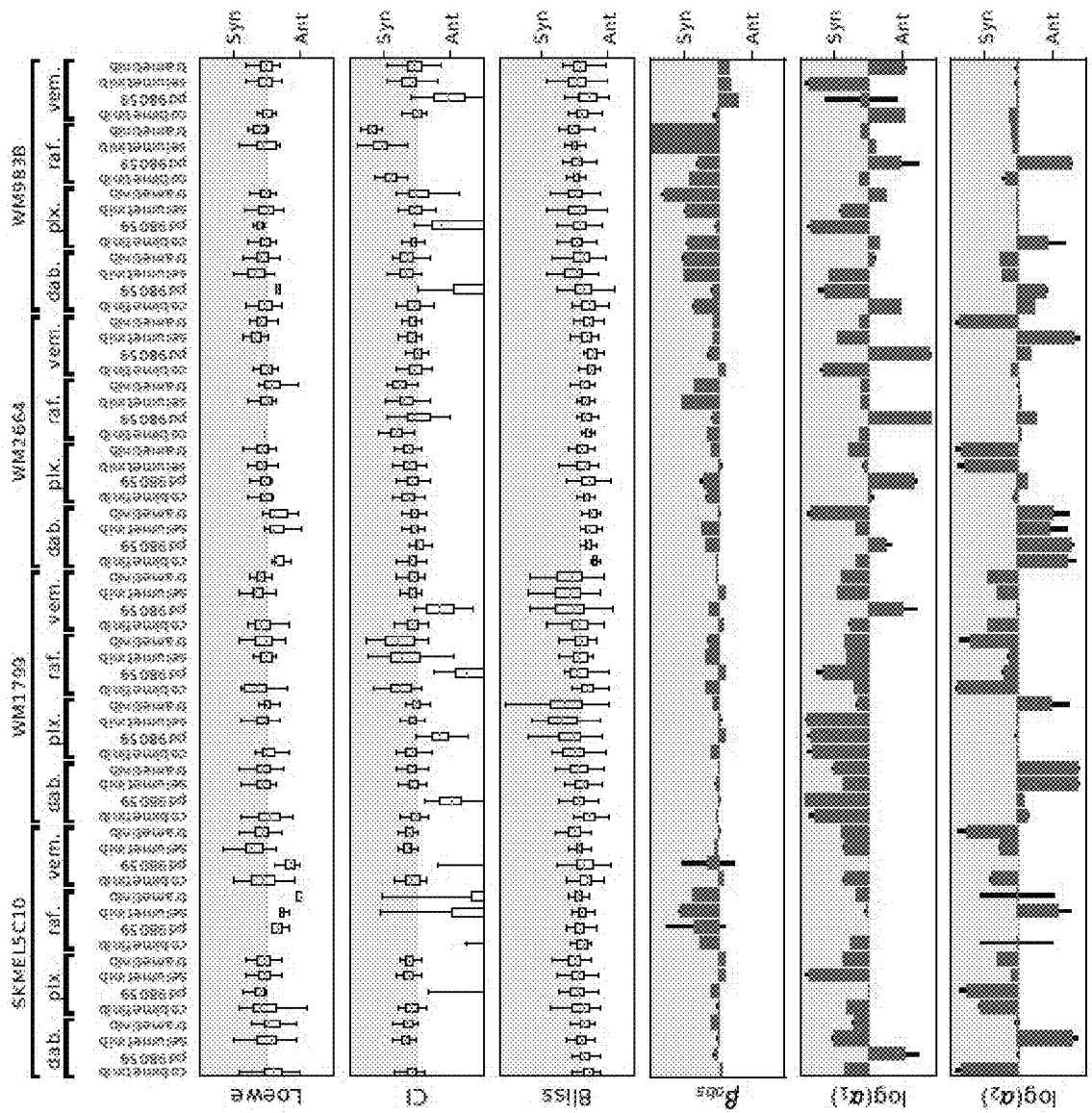
Figure 3-S6B

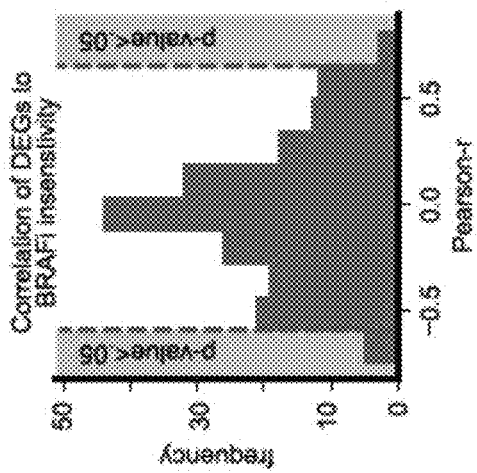
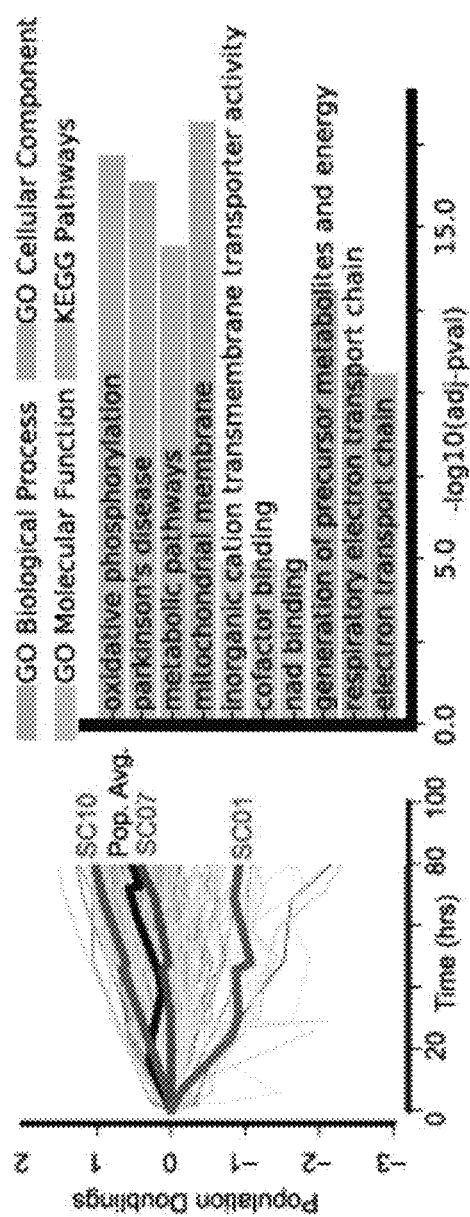
Figure 4A
Figure 4B
Figure 4C

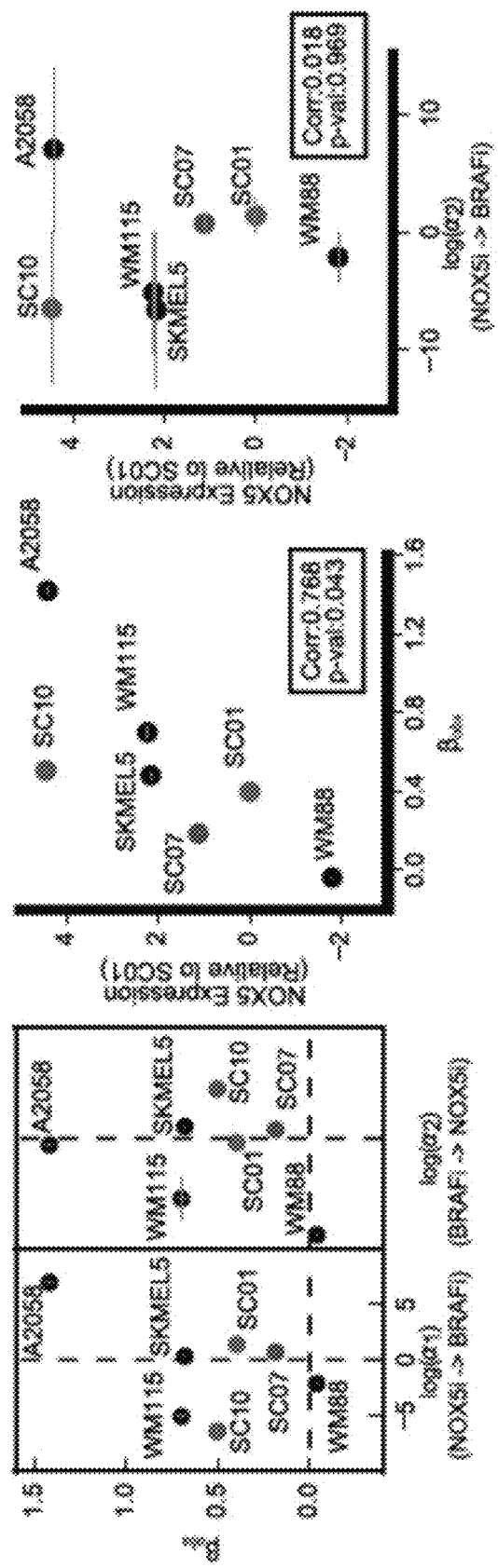

METHODS FOR EVALUATING THERAPEUTIC BENEFIT OF COMBINATION THERAPIES

RELATED APPLICATIONS

This application claims the benefit of U.S. Provisional Patent Application No. 62/978,530, filed Feb. 19, 2020, entitled "METHODS FOR EVALUATING THERAPEUTIC BENEFIT OF COMBINATION THERAPIES," the entire contents of which are incorporated herein by reference.

STATEMENT REGARDING FEDERALLY SPONSORED RESEARCH

This invention was made with government support under contracts U54-CA217450, U54-CA113007, R01-CA186193, and U01-CA215845 awarded by the National Institutes of Health and under contract 1445197 awarded by the National Science Foundation. The government has certain rights in the invention.

FIELD OF THE INVENTION

The invention provides methods for evaluating the therapeutic benefit of a combination therapy useful for treating a medical disorder, such as cancer.

BACKGROUND

Combination therapy is a useful approach to treating medical disorders in which two or more therapeutic agents are used in combination to desirably achieve an effect beyond that provided by each therapeutic agent independently. Combination therapy is frequently utilized in the treatment of different types of cancer, immunological and inflammatory diseases, cardiovascular diseases, viral infections, and bacterial infections. The use of multiple therapeutic agents may target different aspects of the medical disorder to provide a superior therapeutic benefit to the patient.

One heretofore unmet challenge in evaluating combination therapy effects is to adequately characterize whether and to what extent the combination therapy provides improved efficacy (i.e., a greater reduction in disease burden, such as greater reduction in tumor volume when treating a tumor) and/or improved potency (i.e., a lower dose of one or more therapeutic agents can be used to achieve the same effect on disease burden). Understanding when a combination therapy provides improved efficacy is useful when the patient suffering from a medical disorder is in need of therapy that provides greater reduction in disease burden, such as greater reduction in tumor volume when treating a tumor. Understanding when a combination therapy provides improved potency is useful when the patient suffering from a medical disorder is in need of therapy providing improved potency, such as when the patient would benefit from receiving a lower dose of a therapeutic agent in order to minimize an adverse side effect due to the therapeutic agent, but while still achieving at least comparable reduction in disease burden compared to the original dose of therapeutic agent (i.e. when a therapy with improved therapeutic index is needed).

Accordingly, the need exists for new methods for evaluating the therapeutic benefit of combination therapies for treating medical disorders, such as cancer. The present invention addresses this need and provides other related advantages.

SUMMARY

The invention provides methods for evaluating the therapeutic benefit of a combination therapy useful for treating a medical disorder, such as cancer. The methods separately analyze (i) the impact on efficacy provided by the combination therapy relative to the efficacy provided by the most efficacious single therapeutic agent when used alone, (ii) the impact on potency of the first therapeutic agent when the first therapeutic agent is used as part of the combination therapy compared to when the first therapeutic agent is used alone and (iii) the impact on potency of the second therapeutic agent when the second therapeutic agent is used as part of the combination therapy compared to when the second therapeutic agent is used alone. The impact on efficacy and impact on potency noted above is desirably an improvement in efficacy and/or potency. However, it is also important to identify where there is a reduction in efficacy and/or potency, particularly across a dosage range where the impact on efficacy and/or potency may vary as a function of the dosage of first therapeutic and/or dosage of second therapeutic agent.

Separately analyzing impact on efficacy and impact on potency allows for better understanding of the impact of a combination therapy towards treating a particular condition. This enables more informed selection of dose and/or identity of the therapeutic agents, in order to maximize improvements in one or both of efficacy and potency. Improvements in efficacy provide the patient with a greater reduction in disease burden, such as greater reduction in tumor volume when treating a tumor. Improvements in potency mean that a lower dose of one or more therapeutic agents can be used to achieve the same effect on disease burden. The reduction in dose of a therapeutic agent can be beneficial where adverse side effects of the therapeutic agent can be attenuated by administering a lower dose of the therapeutic agent. These and other features and benefits of the method are described in more detail herein below.

One aspect of the invention provides a method for evaluating the therapeutic benefit of a combination therapy comprising a first therapeutic agent and a second therapeutic to be used in combination to treat a medical disorder. Therapeutic benefit is a measure of the overall benefit provided to the patient suffering from the medical disorder. This includes consideration of efficacy of the combination therapy, potency of therapeutic agents as when used in the combination therapy, and optionally (i) safety and toxicity of the combination therapy such as evaluated through therapeutic index of the combination therapy, (ii) risk of the patient developing resistance to the therapy, and (iii) potential for drug-drug interactions between (a) components of the combination therapy and (b) other medicines the patient may be taking for other medical disorders or may take in the future to treat or prevent another medical disorders.

Accordingly, one aspect of the invention provides a method for evaluating the therapeutic benefit of a combination therapy comprising a first therapeutic agent and a second therapeutic to be used in combination to treat a medical disorder, wherein the method comprises the steps of:

(a) determining a difference in efficacy towards the medical disorder between (i) the combination and (ii) the most efficacious single therapeutic agent in the combination;
(b) determining a difference in potency towards the medical disorder for the first therapeutic agent between when (i) the first therapeutic agent is used alone and (ii) the first therapeutic agent is used in combination with the second therapeutic agent; and
(c) determining a difference in potency towards the medical disorder for the second therapeutic agent between when (i) the second therapeutic agent is used alone and (ii) the second therapeutic agent is used in combination with the first therapeutic agent.

Information from steps (a), (b), and (c) may be cross-referenced to understand trends in therapeutic benefit according to the dose of first therapeutic agent, dose of second therapeutic agent, identity of the first therapeutic agent, and/or identity of the second therapeutic agent. For example, in certain embodiments, step (a) comprises determining, across a dosage range for each therapeutic agent in the combination, the difference in efficacy towards the medical disorder between (i) the combination and (ii) the most efficacious single therapeutic agent in the combination. In certain embodiments, step (b) comprises determining, across a dosage range for the first therapeutic agent, the difference in potency towards the medical disorder for the first therapeutic agent between when (i) the first therapeutic agent is used alone and (ii) the first therapeutic agent is used in combination with the second therapeutic agent. In certain embodiments, step (c) comprises determining, across a dosage range for the second therapeutic agent, the difference in potency towards the medical disorder for the second therapeutic agent between when (i) the second therapeutic agent is used alone and (ii) the second therapeutic agent is used in combination with the first therapeutic agent.

Results of information compiled from steps (a), (b), and (c) may be displayed graphically to show trends in potency and efficacy for the combination. For example, in certain embodiments, results from determining the difference in efficacy towards the medical disorder from step (a) are cross-referenced with results from one or both of:
 (i) results from determining the difference in potency towards the medical disorder for the first therapeutic agent from step (b), and
 (ii) results from determining the difference in potency for the second therapeutic agent from step (c);
to generate a graphical display of therapeutic effect according to the dose of first therapeutic agent and dose of second therapeutic agent.

In certain embodiments, the method for evaluating the therapeutic benefit of a combination therapy comprises determining a therapeutic effect (Ed) towards the medical disorder for the combination therapy, at a given concentration of first therapeutic agent and second therapeutic agent, using Equation 1:

$$E_d = \frac{C_1^{h_1} C_2^{h_2} E_0 + d_1^{h_1} C_2^{h_2} E_1 + C_1^{h_1} d_2^{h_2} E_2 + (\alpha_2 d_1)^{h_1} d_2^{h_2} E_3}{C_1^{h_1} C_2^{h_2} + d_1^{h_1} C_2^{h_2} + C_1^{h_1} d_2^{h_2} + (\alpha_2 d_1)^{h_1} d_2^{h_2}} \quad \text{(Equation 1)}$$

wherein the variables are as defined in the detailed description.

In certain embodiments, the method evaluating the therapeutic benefit of a combination therapy comprises determining a therapeutic effect (Ed) towards the medical disorder for the combination therapy, at a given concentration of first therapeutic agent and second therapeutic agent, using Equation 2:

$$E_d = [E_0 E_1 E_2 E_3] \cdot \begin{bmatrix} -(r_1 d_1^{h_1} + r_2 d_2^{h_2}) & r_{-1} & r_{-2} & 0 \\ r_1 d_1^{h_1} & -(r_{-1} + r_2(\alpha_1 d_2)^{h_2}) & 0 & r_{-2} \\ r_2 d_2^{h_2} & 0 & -(r_1(\alpha_2 d_1)^{h_1} + r_{-2}) & r_{-1} \\ 1 & 1 & 1 & 1 \end{bmatrix}^{-1} \cdot \begin{bmatrix} 0 \\ 0 \\ 0 \\ 1 \end{bmatrix} \quad \text{(Equation 2)}$$

wherein the variables are as defined in the detailed description.

In addition to the foregoing, the method can further comprise, for example, evaluating patient biological pathways impacted by all therapeutic agents in the combination therapy. Combination therapies that act on parallel biological pathways may provide greater therapeutic benefit since multiple pathways leading to a biological outcome are inhibited by therapeutic agents in the combination therapy.

In addition to the foregoing, the method can further comprise, for example, evaluating patient cell types impacted by all therapeutic agents in the combination therapy. Combination therapies that act on different cell types may provide greater therapeutic benefit since different cell types leading to a biological outcome are impacted by therapeutic agents in the combination therapy. For example, in the case of cancer, one therapeutic agent may impact cancer cells, and another therapeutic agent may impact one or more immune-system cell types.

In addition to the foregoing, the method can further comprise, for example, evaluating the dosing regimen of the first therapeutic agent, evaluating the dosing regimen of the second therapeutic agent, or evaluating the dosing regimen of all therapeutic agents in the combination therapy.

In addition to the foregoing, the method can further comprise, for example, evaluating the therapeutic index of the first therapeutic agent, evaluating the therapeutic index of the second therapeutic agent, or evaluating the therapeutic index of all therapeutic agents in the combination therapy. Combination therapies that provide sufficient relief from the subject medical disorder, while providing a high margin of safety (e.g., where the combination therapy has a high therapeutic index) provide greater therapeutic benefit to the patient. In relevant part, the patient experiences less risk of an adverse event when the combination therapy has a high therapeutic index.

In addition to the foregoing, the method can further comprise, for example, analyzing a biological sample from a patient suspected of suffering from the medical disorder. This may reveal that the patient has a mutation for which a particular therapeutic agent will provide superior potency and/or efficacy. Having knowledge of the foregoing, enables selecting the identity of at least one therapeutic agent in the combination therapy based on a feature of a biological sample obtained from a patient suspected of suffering from the medical disorder. In certain embodiments, the feature may be a cancer mutation.

In addition to the foregoing, the method can further comprise, for example, evaluating the oxidation state of a biological pathway impacting the medical disorder. The oxidation state of a biological pathway can inform which therapeutic agents may provide the greatest potency and/or efficacy against a medical disorder. For example, a cancer featuring elevated oxidation state may be more effectively treated by administering a therapeutic agent that lowers the oxidation state of the cancer tissue. In certain embodiments, the method further comprises selecting the identity of at least one therapeutic agent in the combination therapy to impact the oxidation state of a biological pathway impacting the medical disorder. In addition to the foregoing, the method can further comprise, for example, evaluating other functional states of a biological pathway impacting the medical disorder.

The methods can be used to guide selection of a particular combination therapy to be used to treat a patient suffering from cancer. In instances where greater efficacy is needed because the patient is experiencing insufficient elimination of cancer cells, combination therapies providing greater efficacy are preferred. In instances where greater potency is needed, such as to reduce the dose of a drug and thereby reduce an adverse event associated with elevated doses of the drug, a combination therapy providing greater potency is preferred. After having selected the particular therapeutic agents to be used in the combination therapy, selection of dose for each therapeutic agent in the combination therapy may be selected based on analysis of changes in efficacy and potency as function of dose of each therapeutic agent in the combination therapy.

The foregoing aspects and embodiments of the invention are described in more detail, along with additional embodiments, in the detailed description below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A, 1B, and 1C depict 2D Hill equation dose-response surfaces, whose parameters distinguish synergistic efficacy and synergistic potency, wherein FIG. 1A depicts sigmoidal dose-response curves relating drug concentration to a measured effect fit to the Hill equation, containing parameters for calculating a drug's potency (C, the concentration required for half-maximal effect) and efficacy ($E_{max}$, the maximal effect). Here, Drug 1 is more potent than Drug 2 (C1<C2), while Drug 2 is more efficacious (E2<E1); FIG. 1B depicts a dose-response surface for Drugs 1 and 2, based on our equation (FIG. 1-S1B), under the null hypothesis of no synergy of efficacy ($\beta$=0) or potency ($\alpha 1=\alpha 2=1$). In FIG. 1B, representative dose-response surfaces for each quadrant are presented on a drug synergy diagram (DSD); the vertical axis is divided into antagonistic ($\beta$<0) and synergistic ($\beta$>0) efficacy; the horizontal axis is divided into antagonistic ($\log(\alpha^*)$<0) and synergistic ($\log(\alpha^*)$>0) potency where $\alpha^*$ can be either $\alpha 1$ or $\alpha 2$; quadrant I corresponds to synergistic potency and efficacy. In contrast, combinations in quadrant IV have synergistic potency but antagonistic efficacy corresponding to a blunting in efficacy at lower doses.

FIG. 1-S1B illustrates aspects of a 4-state model of drug combination action. The equilibrium between the percent of cell affected by Drug 1 or Drug 2 alone ($A_1$ and $A_2$, respectively) and the doubly affected ($A_{12}$) populations is governed by the concentration of Drug 1 modulated by $\alpha_2$ (which quantifies Drug 2's action on the potency of Drug 1) and by the converse, Drug 2 multiplied by $\alpha_1$. E3 represents the maximal effect of the combination.

FIG. 1-S1C depicts drug combination dose-response surfaces with asymmetric synergistic potency ($\alpha_1$>1, $\alpha_2$<1). The three surfaces correspond to the following conditions (from left to right): combination with asymmetric potency and no synergistic efficacy (E1=E2=E3); combination with asymmetric synergistic potency with synergistic efficacy (min(E1,E2)>E3); combination with asymmetric synergistic potency with antagonistic efficacy (min(E1,E2)<E3).

FIGS. 2B and 2C depict drug combination dose-response surfaces for osimertinib and M344 (an HDAC inhibitor, FIG. 2B) or ceritinib ("cer", an ALK inhibitor, FIG. 2C). The gray plane indicates a cytostatic growth rate (i.e., DIP rate=0 $h^{-1}$). The inset plots are the dose-response curves for each drug alone (orange and red curves) and each drug with the maximum tested concentration of the other (green and purple curves). Colors correspond to the colored lines on the edges of the combination surface. The dotted lines demarcate the $EC_{50}$ for each curve.

FIG. 3-S4A depicts a Jitter plot of the 64 surveyed single drug's $E_{max}$(obs), C [μM], and Hill slope h.

FIG. 3-S4B depicts graphs showing that synergy parameters do not correlate (Pearson-r) with a single drug's potency and efficacy in isolation (where $\alpha_2$ describes X potentiating osimertinib).

FIG. 3-S5 depicts synergistic potency, synergistic efficacy, and maximal effect of combined RAF and MEK inhitors (RAFi and MEKi). Panel A depicts Jitter plots of $\log(\alpha_1)$ for each RAFi for the 4 MEKi tested. $\alpha_1$ corresponds to the alteration in the MEKi's effective dose due to the presence of the RAFi. The dashed line denotes zero, which separates synergistic and antagonistic potency. The color of the plotted points corresponds to the cell line as annotated at the bottom of the figure (e.g., A2058, A375, etc.). Panel B depicts Jitter plots of log($\alpha_2$) for each MEKi for the 4 RAFi tested. $\alpha_2$ corresponds to the alteration in the RAF inhibitor's effective dose due to the presence of the MEK inhibitor. Panel C depicts rank-ordered jitter plots of the median $\beta_{obs}$ for each drug combination across all cell lines. Panel D depicts distribution of maximal effects for RAFi alone (E1, 4 drugs), MEKi alone (E2, 4 drugs), and the combination (E3, 16 combinations), for each cell line. Each orange bar denotes the mean.

FIGS. 3-S6A and 3-S6B depict errors reported by other methods for describing drug synergy (Loewe, CI, and Bliss; top 3 panels), when applied to the melanoma dataset. Loewe was calculated directly from DIP rates, while CI and Bliss were calculated from 72-hour viability. Conditions for which synergy is undefined were not included. By these traditional methods, combinations of BRAF/MEK inhibitors in melanoma are ambiguous, spanning synergy (Syn-gray) and antagonism (Ant-white). MuSyC parameters are displayed in the bottom three panels. Log($\alpha_1$) is the RAFi's effect on the potency of the MEKi, and log($\alpha_2$) is the reverse. Abbreviations of the RAF inhibitors are: dab=dabrafenib, plx=plx4720, raf=raf265, and vem=vemurafenib.

FIGS. 4A, 4B, and 4C depict data used to identify and characterize the top 200 differentially expressed genes (DEGs) between subclones of a BRAF-mutant melanoma cell line (SKMEL5) with differential sensitivity to BRAFi. FIG. 4A depicts growth curves of differentially sensitive, single-cell-derived subclones from SKMEL5 treated with 8 µM PLX4720. Gray curves represent colony growth according to the clonal fractional proliferation assay (Tyson, D. R. et al., *Nature Methods* (2012) Vol. 9, pp. 923-928). The average population response is indicated in the black curve. SC01, SC07, and SC10 were subsequently used to identify 200 DEGs. FIG. 4B depicts the top gene set enrichment terms for the identified 200 DEGs. FIG. 4C depicts a distribution of the correlation between the identified 200 DEGs' expression and BRAFi insensitivity. Drug sensitivity was quantified as DIP rate measured in 8 µM PLX4720. The threshold of p value <0.05 is annotated in pink.

FIG. 4D is a graph demonstrating that NOX5 expression correlates with BRAFi sensitivity in 10 BRAF-mutant melanoma cells. FIG. 4E depicts pairwise comparison between SC01 and SC10 of DEGs (FDR<0.001) identified using DESeq2 (Love, M. I. et al., *Genome Biol.* (2014) Vol. 15, p. 550). The 200 identified DEGs (ANOVA between three subclones) are in black. The dotted red lines denote ±4-fold change. FIG. 4F depicts the dose-response surface for PLX4270 plus DPI (a NOX5 inhibitor) in the A2058 cell line, using the same format as in FIGS. 2B and 2C.

FIGS. 4G, 4H, and 4I depict additional MuSyC analysis of the effect of the combination therapy with PLX4270 and DPI. FIG. 4G depicts a DSD for NOX5i (DPI) plus BRAFi (PLX4720). FIG. 4H depicts the correlation (Pearson r) of NOX5 expression with observed synergistic efficacy ($\beta_{obs}$). FIG. 4I depicts the correlation (Pearson r) of NOX5 expression with synergistic potency, where $\alpha_2$ is DPI's effect on PLX4720 potency. Error bars represent parameter uncertainty calculated in MCMC fitting.

DETAILED DESCRIPTION

Figure 2A:
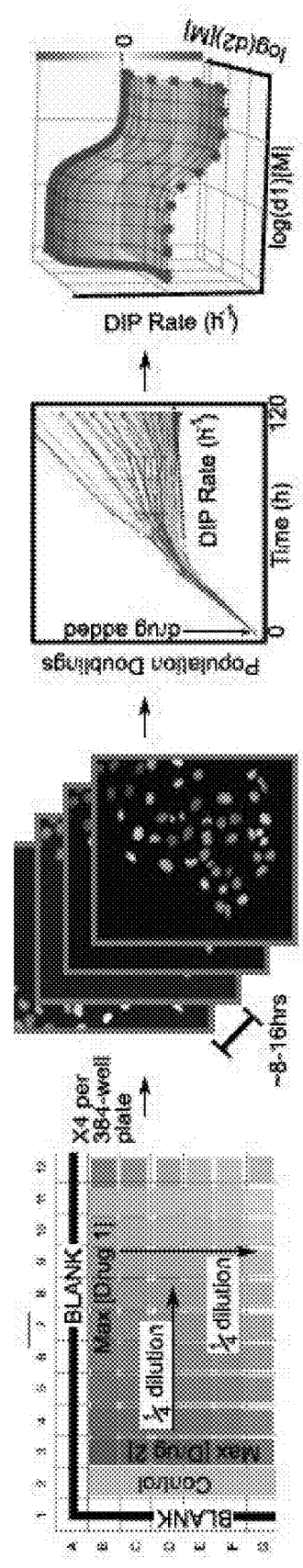
FIG. 2A illustrates a high-throughput pipeline for generating dose-response surfaces. Initial drug matrix is prepared on a 384-well plate and transferred to cells seeded at subconfluent densities. Cells are engineered to express a fluorescently tagged histone (H2B-RFP), allowing for cell counts using automated segmentation software. Each condition is imaged every 6-8 h, resulting in growth curves. The growth curves are fit to determine the drug-induced proliferation (DIP) rate (slope of dotted line, vide infra) to quantify drug effect. This matrix of DIP rates is fit to our equation to extract synergy parameters.
Figure 2D:
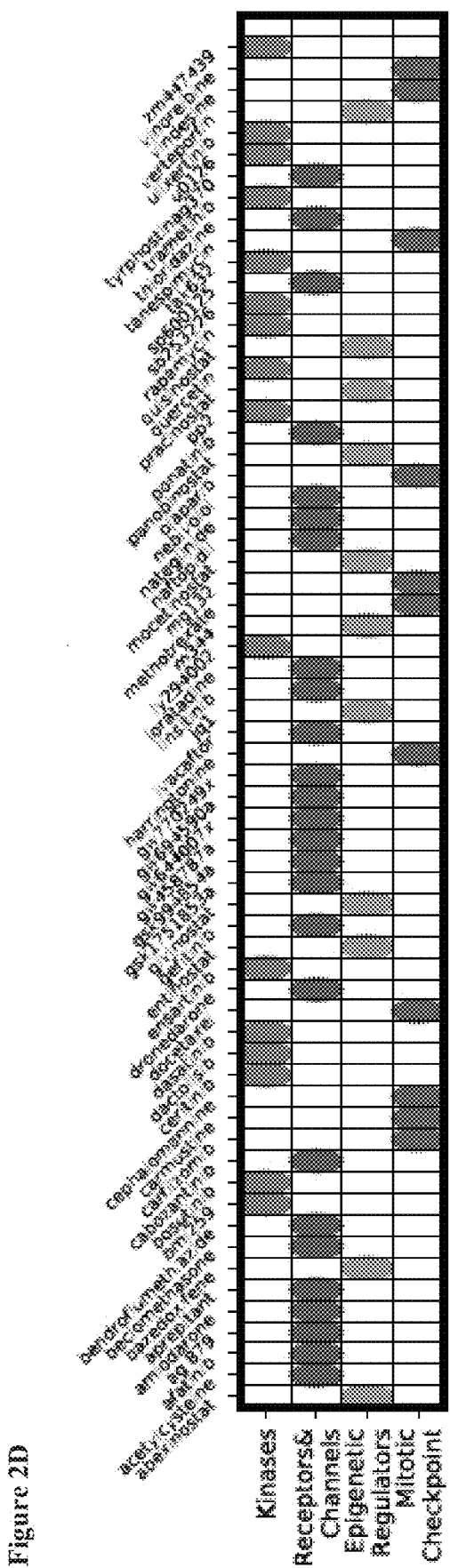
FIG. 2D illustrates a drug panel used in combination with osimertinib grouped into 4 categories.

The invention provides methods for evaluating the therapeutic benefit of a combination therapy useful for treating a medical disorder, such as cancer. The methods separately analyze (i) the impact on efficacy provided by the combination therapy relative to the efficacy provided by the most efficacious single therapeutic agent when used alone, (ii) the impact on potency of the first therapeutic agent when the first therapeutic agent is used as part of the combination therapy compared to when the first therapeutic agent is used alone and (iii) the impact on potency of the second therapeutic agent when the second therapeutic agent is used as part of the combination therapy compared to when the second therapeutic agent is used alone. The impact on efficacy and impact on potency noted above is desirably an improvement in efficacy and/or potency. However, it is also important to identify where there is a reduction in efficacy and/or potency, particularly across a dosage range where the impact on efficacy and/or potency may vary as a function of the dosage of first therapeutic and/or dosage of second therapeutic agent.

Separately analyzing impact on efficacy and impact on potency allows for better understanding of the impact of a combination therapy towards treating a particular condition. This enables more informed selection of dose and/or identity of the therapeutic agents, in order to maximize improvements in one or both of efficacy and potency. Improvements in efficacy provide the patient with a greater reduction in disease burden, such as greater reduction in tumor volume when treating a tumor. Improvements in potency mean that a lower dose of one or more therapeutic agents can be used to achieve the same effect on disease burden. The reduction in dose of a therapeutic agent can be beneficial where adverse side effects of the therapeutic agent can be attenuated by administering a lower dose of the therapeutic agent. These and other features and benefits of the method are described in more detail herein below.

The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section.

I. Definitions

To facilitate an understanding of the present invention, a number of terms and phrases are defined below.

The terms "a," "an" and "the" as used herein mean "one or more" and include the plural unless the context is inappropriate The term "about" means within 10% of the stated value. In certain embodiments, the value may be within 8%, 6%, 4%, 2%, or 1% of the stated value.

As used herein, the term "efficacy" refers to the extent of reduction in disease burden against a medical disorder achieved with a given therapy (e.g., treatment with a single therapeutic agent or a combination therapy). Efficacy is measured for quantifiable impact of the therapy on disease burden due to the medical disorder. For example, efficacy against cancer can be determined based upon the in vitro drug-induced proliferation (DIP) rate (see, Harris, L. A., et al. "An unbiased metric of antiproliferative drug effect in vitro," *Nature Methods,* 2016, vol. 13, p. 497-500), in vitro cell proliferation, or in vivo tumor volume (e.g., in a xenograft model or in actual patients).

In the context of describing the most efficacy therapeutic agent in a combination therapy, the term "most efficacious" refers to the therapeutic agent within a group of therapeutic agents that displays the greatest efficacy.

As used herein, the term "potency" refers to the dose of therapeutic agent(s) required to achieve a specified effect. One measure of potency is the dose of therapeutic agent required to achieve half the maximum extent of treatment of a medical disorder achieved with a given therapy (e.g., treatment with a single therapeutic agent or a combination therapy), classically described as the $EC_{50}$, or as the dose of therapeutic agent required to achieve the maximum extent of treatment of a medical disorder. The potency may alternatively be defined using other specified effects appropriate for a given assay or medical disorder, for example, the $IC_{50}$ for an enzyme inhibition assay, the minimum inhibitory concentration for an antibacterial assay, or the $IC_{90}$ for an anti-viral assay.

As used herein, the term "patient" refers to organisms to be treated by the methods of the present invention. Such organisms preferably include, but are not limited to, mammals (e.g., murines, simians, equines (horses), bovines (cattle), porcines, canines, felines, and the like), and most preferably includes humans.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "therapeutically effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route.

As used herein, the term "pharmaceutical composition" refers to the combination of an active agent with a carrier, inert or active, making the composition especially suitable for diagnostic or therapeutic use in vivo or ex vivo.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to any of the standard pharmaceutical carriers. The compositions also can include stabilizers and preservatives. For examples of carriers, stabilizers, and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Further examples of salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Still other examples of salts include anions of the compounds of the present invention compounded with a suitable cation such as $Na^+$, $NH_4^+$, and $NW_4^+$ (wherein W is a $C_{1-4}$ alkyl group), and the like. The term "alkyl" is art-recognized, and includes saturated aliphatic groups, including straight-chain alkyl groups and branched-chain alkyl groups.

Throughout the description, where processes and methods are described as having, including, or comprising specific steps, it is contemplated that, additionally, there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Methods For Evaluating Therapeutic Benefit of a Combination Therapy

The invention provides methods for evaluating the therapeutic benefit of a combination therapy useful for treating a medical disorder, such as cancer. The methods separately analyze (i) the impact on efficacy provided by the combination therapy relative to the efficacy provided by the most efficacious single therapeutic agent when used alone, (ii) the impact on potency of the first therapeutic agent when the first therapeutic agent is used as part of the combination therapy compared to when the first therapeutic agent is used alone and (iii) the impact on potency of the second therapeutic agent when the second therapeutic agent is used as part of the combination therapy compared to when the second therapeutic agent is used alone. The impact on efficacy and impact on potency noted above is desirably an improvement in efficacy and/or potency. However, it is also important to identify where there is a reduction in efficacy and/or potency, particularly across a dosage range where the impact on efficacy and/or potency may vary as a function of the dosage of first therapeutic and/or dosage of second therapeutic agent. The methods are described in more detail below.

One aspect of the invention provides a method for evaluating the therapeutic benefit of a combination therapy comprising a first therapeutic agent and a second therapeutic to be used in combination to treat a medical disorder. The method comprises the steps of:
  (a) determining a difference in efficacy towards the medical disorder between (i) the combination and (ii) the most efficacious single therapeutic agent in the combination;
  (b) determining a difference in potency towards the medical disorder for the first therapeutic agent between when (i) the first therapeutic agent is used alone and (ii) the first therapeutic agent is used in combination with the second therapeutic agent; and
  (c) determining a difference in potency towards the medical disorder for the second therapeutic agent between when (i) the second therapeutic agent is used alone and (ii) the second therapeutic agent is used in combination with the first therapeutic agent.

The method may be further characterized according to one more of the general features described herein below.

General Features

The above method may be further characterized by additional features, such as the doses or dosage range of each therapeutic agent used in the determinations in steps (a), (b), and (c); whether the results of step (a) are cross-referenced with the results of step (b) and/or (c); and selecting a dosage amount for at least one therapeutic agent based upon, and/or selecting the identity of at least one therapeutic agent based upon additional characteristics of the therapeutic agent(s), such as the pharmacokinetic properties, safety profile, and toxicity profile.

Doses of Therapeutic Agents Used in the Determinations of Steps (a), (b), and (c)

The therapeutic method can be further characterized according to the doses or dosage ranges of each of the therapeutic agents used in the determinations of steps (a), (b), and (c). For example, in certain embodiments, step (a) comprises determining, for a plurality of different doses for each therapeutic agent in the combination, the difference in efficacy towards the medical disorder between (i) the combination and (ii) the most efficacious single therapeutic agent in the combination. In certain embodiments, step (a) comprises determining, across a dosage range for each therapeutic agent in the combination, the difference in efficacy towards the medical disorder between (i) the combination and (ii) the most efficacious single therapeutic agent in the combination.

In certain embodiments, step (b) comprises determining, for a plurality of different doses of the first therapeutic agent, the difference in potency towards the medical disorder for the first therapeutic agent between when (i) the first therapeutic agent is used alone and (ii) the first therapeutic agent is used in combination with the second therapeutic agent. In certain embodiments, step (b) comprises determining, across a dosage range for the first therapeutic agent, the difference in potency towards the medical disorder for the first therapeutic agent between when (i) the first therapeutic agent is used alone and (ii) the first therapeutic agent is used in combination with the second therapeutic agent.

In certain embodiments, step (b) comprises determining, for a plurality of different doses of the second therapeutic agent, the difference in potency towards the medical disorder for the first therapeutic agent between when (i) the first therapeutic agent is used alone and (ii) the first therapeutic agent is used in combination with the second therapeutic agent. In certain embodiments, step (b) comprises determining, across a dosage range for the second therapeutic agent, the difference in potency towards the medical disorder for the first therapeutic agent between when (i) the first therapeutic agent is used alone and (ii) the first therapeutic agent is used in combination with the second therapeutic agent.

In certain embodiments, step (c) comprises determining, for a plurality of different doses of the second therapeutic agent, the difference in potency towards the medical disorder for the second therapeutic agent between when (i) the second therapeutic agent is used alone and (ii) the second therapeutic agent is used in combination with the first therapeutic agent. In certain embodiments, step (c) comprises determining, across a dosage range for the second therapeutic agent, the difference in potency towards the medical disorder for the second therapeutic agent between when (i) the second therapeutic agent is used alone and (ii) the second therapeutic agent is used in combination with the first therapeutic agent.

In certain embodiments, step (c) comprises determining, for a plurality of different doses of the first therapeutic agent, the difference in potency towards the medical disorder for the second therapeutic agent between when (i) the second therapeutic agent is used alone and (ii) the second therapeutic agent is used in combination with the first therapeutic agent. In certain embodiments, step (c) comprises determining, across a dosage range for the first therapeutic agent, the difference in potency towards the medical disorder for the second therapeutic agent between when (i) the second therapeutic agent is used alone and (ii) the second therapeutic agent is used in combination with the first therapeutic agent.

Cross-Referencing Results of Step (a) with Results of Step (b) and/or (c)

The therapeutic method can be further characterized according to whether the results of step (a) are cross-referenced with the results of step (b) and/or (c). For example, in certain embodiments, results from determining the difference in efficacy from step (a) are cross-referenced with results from one or both of:
  (i) results from determining the difference in potency towards the medical disorder for the first therapeutic agent from step (b), and
  (ii) results from determining the difference in potency towards the medical disorder for the second therapeutic agent from step (c).

In certain embodiments, results from determining the difference in efficacy from step (a) are cross-referenced with results from both:
  (i) results from determining the difference in potency towards the medical disorder for the first therapeutic agent from step (b), and (ii) results from determining the difference in potency towards the medical disorder for the second therapeutic agent from step (c).

In certain embodiments, results from determining the difference in efficacy from step (a) are cross-referenced with results from one or both of:
  (i) results from determining the difference in potency towards the medical disorder for the first therapeutic agent from step (b), and
  (ii) results from determining the difference in potency towards the medical disorder for the second therapeutic agent from step (c);
to generate a graphical display of therapeutic effect according to the dose of first therapeutic agent and dose of second therapeutic agent. In certain embodiments, results from determining the difference in efficacy from step (a) are cross-referenced with results from both:
  (i) results from determining the difference in potency towards the medical disorder for the first therapeutic agent from step (b), and
  (ii) results from determining the difference in potency towards the medical disorder for the second therapeutic agent from step (c);
to generate a graphical display of therapeutic effect according to the dose of first therapeutic agent and dose of second therapeutic agent.

Use of Equation 1

In certain embodiments, the method comprises determining a therapeutic effect ($E_d$) towards the medical disorder for the combination therapy, at a given concentration of first therapeutic agent and second therapeutic agent, using Equation 1:

$$E_d = \frac{C_1^{h_1} C_2^{h_2} E_0 + d_1^{h_1} C_2^{h_2} E_1 + C_1^{h_1} d_2^{h_2} E_2 + (\alpha_2 d_1)^{h_1} d_2^{h_2} E_3}{C_1^{h_1} C_2^{h_2} + d_1^{h_1} C_2^{h_2} + C_1^{h_1} d_2^{h_2} + (\alpha_2 d_1)^{h_1} d_2^{h_2}} \quad \text{(Equation 1)}$$

wherein:
$C_1$ is the concentration of the first therapeutic agent required to achieve 50% of the maximum efficacy of the combination therapy towards the medical disorder;
$C_2$ is the concentration of the second therapeutic agent required to achieve 50% of the maximum efficacy of the combination therapy towards the medical disorder;
$h_1$ is the Hill coefficient for the dose-response curve of the first therapeutic agent when the first therapeutic agent is used alone;
$h_2$ is the Hill coefficient for the dose-response curve of the second therapeutic agent when the second therapeutic agent is used alone;
$d_1$ is concentration of the first therapeutic agent;
$d_2$ is concentration of the second therapeutic agent;

$E_0$ is the basal effect (i.e., the efficacy when neither the first nor second therapeutic agent is used to treat the medical disorder);
$E_1$ is the maximum efficacy towards the medical disorder of the first therapeutic agent when the first therapeutic agent is used alone;
$E_2$ is the maximum efficacy towards the medical disorder of the second therapeutic agent when the second therapeutic agent is used alone;
$E_3$ is the maximum efficacy towards the medical disorder of the combination therapy; and
$\alpha_2$ is the fold-change in the concentration of the first therapeutic agent required to achieve 50% of the maximum efficacy towards the medical disorder of the combination therapy compared to when the first therapeutic agent is used alone.

In certain embodiments, the therapeutic agents in the combination therapy obey detailed balance.

Use of Equation 2

In certain embodiments, the method comprises determining a therapeutic effect ($E_d$) towards the medical disorder for the combination therapy, at a given concentration of first therapeutic agent and second therapeutic agent, using Equation 2:

$$E_d = [E_0 E_1 E_2 E_3] \cdot \begin{bmatrix} -(r_1 d_1^{h_1} + r_2 d_2^{h_2}) & r_{-1} & r_{-2} & 0 \\ r_1 d_1^{h_1} & -(r_{-1} + r_2(\alpha_1 d_2)^{h_2}) & 0 & r_{-2} \\ r_2 d_2^{h_2} & 0 & -(r_1(\alpha_2 d_1)^{h_1} + r_{-2}) & r_{-1} \\ 1 & 1 & 1 & 1 \end{bmatrix}^{-1} \begin{bmatrix} 0 \\ 0 \\ 0 \\ 1 \end{bmatrix} \quad \text{(Equation 2)}$$

wherein:
$C_1$ is the concentration of the first therapeutic agent required to achieve 50% of the maximum efficacy of the combination therapy towards the medical disorder;
$C_2$ is the concentration of the second therapeutic agent required to achieve 50% of the maximum efficacy of the combination therapy towards the medical disorder;
$h_1$ is the Hill coefficient for the dose-response curve of the first therapeutic agent when the first therapeutic agent is used alone;
$h_2$ is the Hill coefficient for the dose-response curve of the second therapeutic agent when the second therapeutic agent is used alone;
$d_1$ is concentration of the first therapeutic agent;
$d_2$ is concentration of the second therapeutic agent;
$E_0$ is the basal effect (i.e., the efficacy when neither the first nor second therapeutic agent is used to treat the medical disorder);
$E_1$ is the maximum efficacy towards the medical disorder of the first therapeutic agent when the first therapeutic agent is used alone;
$E_2$ is the maximum efficacy towards the medical disorder of the second therapeutic agent when the second therapeutic agent is used alone;
$E_3$ is the maximum efficacy towards the medical disorder of the combination therapy;

$\alpha_1$ is the fold-change in the concentration of the second therapeutic agent required to achieve 50% of the maximum efficacy towards the medical disorder of the combination therapy compared to when the second therapeutic agent is used alone;

$\alpha_2$ is the fold-change in the concentration of the first therapeutic agent required to achieve 50% of the maximum efficacy towards the medical disorder of the combination therapy compared to when the first therapeutic agent is used alone;

$r_1$ is the rate of transition for the first therapeutic agent from the unaffected state to the affected state;

$r_{-2}$ is $r_1 * C_1^{h1}$;

$r_2$ is the rate of transition for the second therapeutic agent from the unaffected state to the affected state; and $r_{-2}$ is $r_2 * C_2^{h2}$.

The unaffected state refers to the activity state the first therapeutic agent in the absence of additional therapeutic agents. The affected state refers to the activity state of the first therapeutic agent in the present of additional therapeutic agents in the combination therapy.

In certain embodiments, the therapeutic agents in the combination therapy do not obey detailed balance.

Doses of Therapeutic Agents Used in the Determinations of Therapeutic Effect ($E_d$)

The methods may be characterized according to the doses or dosage ranges of each of the therapeutic agents used in the determinations of the therapeutic effect ($E_d$). For instance, in certain embodiments, the therapeutic effect ($E_d$) is determined at a plurality of different doses for the first therapeutic agent. In certain embodiments, the therapeutic effect ($E_d$) is determined across a dosage range for the first therapeutic agent. In certain embodiments, the therapeutic effect ($E_d$) is determined at a plurality of different doses for the second therapeutic agent. In certain embodiments, the therapeutic effect ($E_d$) is determined across a dosage range for the second therapeutic agent.

Methods Employed in Calculating the Therapeutic Effect ($E_d$)

The methods may be further characterized according to the methods employed in calculating the therapeutic effect ($E_d$). For instance, in certain embodiments, a curve fitting algorithm is used to calculate the therapeutic effect ($E_d$). In certain embodiments, the curve fitting algorithm is a Bayesian fitting algorithm. In certain embodiments, the curve fitting algorithm is a Bayesian fitting algorithm using a particle swarm optimizer to seed priors for a Markov chain Monte Carlo optimization. In certain embodiments, the curve fitting algorithm comprises use of a neural network.

Methods of Displaying the Therapeutic Effect ($E_d$)

The methods may be further characterized according to the methods of displaying the therapeutic effect ($E_d$). For instance, in certain embodiments, the therapeutic effect ($E_d$) is displayed graphically according to the determined therapeutic effect ($E_d$) across different doses for the first therapeutic agent. In certain embodiments, the therapeutic effect ($E_d$) is displayed graphically according to the determined therapeutic effect ($E_d$) across a dosage range for the first therapeutic agent. In certain embodiments, the therapeutic effect ($E_d$) is displayed graphically according to the determined therapeutic effect ($E_d$) across different doses for the second therapeutic agent. In certain embodiments, the therapeutic effect ($E_d$) is displayed graphically according to the determined therapeutic effect ($E_d$) across a dosage range for the second therapeutic agent.

Evaluating Pharmacokinetic Profiles

The methods may be further characterized according to whether the method further comprises evaluating the pharmacokinetic properties of at least one of the therapeutic agents. For example, in certain embodiments, the method further comprises evaluating the pharmacokinetic properties of at least one of the therapeutic agents. In certain embodiments, the method further comprises evaluating the pharmacokinetic properties of the first therapeutic agent. In certain embodiments, the method further comprises evaluating the pharmacokinetic properties of the second therapeutic agent. In certain embodiments, the method further comprises evaluating the pharmacokinetic properties of all therapeutic agents in the combination therapy.

In certain embodiments, the method further comprises selecting a dosage amount for at least one therapeutic agent in the combination therapy to improve the therapeutic benefit of the combination in view of the pharmacokinetic properties. In certain embodiments, the method further comprises selecting a dosage amount for each therapeutic agent in the combination therapy to improve the therapeutic benefit of the combination in view of pharmacokinetic properties of each therapeutic agent. In certain embodiments, the method further comprises selecting the identity of at least one therapeutic agent in the combination therapy in order to improve the therapeutic benefit of the combination in view of pharmacokinetic properties of the therapeutic agent. In certain embodiments, the method further comprises selecting the identity of each therapeutic agent in the combination therapy in order to improve the therapeutic benefit of the combination in view of pharmacokinetic properties of each therapeutic agent.

Evaluating Dosing Regimen

The methods may be further characterized according to whether the method further comprises evaluating the dosing regimen of at least one of the therapeutic agents. For example, in certain embodiments, the method further comprises evaluating the dosing regimen of at least one of the therapeutic agents. In certain embodiments, the method further comprises evaluating the dosing regimen of the first therapeutic agent. In certain embodiments, the method further comprises evaluating the dosing regimen of the second therapeutic agent. In certain embodiments, the method further comprises evaluating the dosing regimens of all therapeutic agents in the combination therapy.

In certain embodiments, the method further comprises selecting a dosing regimen for at least one therapeutic agent in the combination therapy to improve the therapeutic benefit of the combination in view of the dosing regimen. In certain embodiments, the method further comprises selecting a dosing regimen for each therapeutic agent in the combination therapy to improve the therapeutic benefit of the combination in view of dosing regimen of each therapeutic agent.

Dosing regimens may be characterized by features such as, for example, the dosing frequency, dosing order, and/or treatment cycle. For example, in certain embodiments, the first therapeutic agent is administered 1, 2, or 3 times per day. In certain embodiments, the first therapeutic agent is administered once per day. In certain embodiments, the second therapeutic agent is administered 1, 2, or 3 times per day. In certain embodiments, the second therapeutic agent is administered once per day.

Components in a combination therapy may be administered in a particular order and/or according to a treatment cycle. For example, in certain embodiments, at least one dose of the first therapeutic agent is administered to the patient prior to administering the second therapeutic agent. In certain embodiments, at least one dose of the first therapeutic agent is administered to the patient prior to administering the second therapeutic agent, but while there remains an effective amount of the first therapeutic agent in the patient. In certain embodiments, all doses of the first therapeutic agent are administered to the patient prior to administering the second therapeutic agent.

In certain embodiments, at least one dose of the second therapeutic agent is administered to the patient prior to administering the first therapeutic agent. In certain embodiments, at least one dose of the second therapeutic agent is administered to the patient prior to administering the first therapeutic agent, but while there remains an effective amount of the second therapeutic agent in the patient. In certain other embodiments, active components of the combination therapy may be co-administered simultaneously. In certain embodiments, all doses of the second therapeutic agent are administered to the patient prior to administering the first therapeutic agent.

In certain other embodiments, active components of the combination therapy may be co-administered in a predetermined manner, ratio, and order of addition so as to comprise a treatment cycle. In certain other embodiments, treatment cycles may be repeated in order to maximize benefit to the patient.

Evaluating Safety Profiles

The methods may be further characterized according to whether the method further comprises evaluating the safety profile of at least one of the therapeutic agents. For example, in certain embodiments, the method further comprises evaluating the safety profile of at least one of the therapeutic agents. In certain embodiments, the method further comprises evaluating the safety profile of the first therapeutic agent. In certain embodiments, the method further comprises evaluating the safety profile of the second therapeutic agent. In certain embodiments, the method further comprises evaluating the safety profile of all therapeutic agents in the combination therapy.

In certain embodiments, the method further comprises selecting a dosage amount for at least one therapeutic agent in the combination therapy that improves the safety profile of the combination therapy. In certain embodiments, the method further comprises selecting a dosage amount for each therapeutic agent in the combination therapy that improves the safety profile of the combination therapy. In certain embodiments, the method further comprises selecting the identity of at least one therapeutic agent in the combination therapy in order to improve the safety profile of the combination therapy. In certain embodiments, the method further comprises selecting the identity of each therapeutic agent in the combination therapy in order to improve the safety profile of the combination therapy.

Evaluating Toxicity Profiles

The methods may be further characterized according to whether the method further comprises evaluating the toxicity profile of at least one of the therapeutic agents. For example, in certain embodiments, the method further comprises evaluating the toxicity profile of at least one of the therapeutic agents. In certain embodiments, the method further comprises evaluating the toxicity profile of the first therapeutic agent. In certain embodiments, the method further comprises evaluating the toxicity profile of the second therapeutic agent. In certain embodiments, the method further comprises evaluating the toxicity profile of all therapeutic agents in the combination therapy.

In certain embodiments, the method further comprises selecting a dosage amount for at least one therapeutic agent in the combination therapy that improves the toxicity profile of the combination therapy. In certain embodiments, the method further comprises selecting a dosage amount for each therapeutic agent in the combination therapy that improves the toxicity profile of the combination therapy. In certain embodiments, the method further comprises selecting the identity of at least one therapeutic agent in the combination therapy in order to improve the toxicity profile of the combination therapy. In certain embodiments, the method further comprises selecting the identity of each therapeutic agent in the combination therapy in order to improve the toxicity profile of the combination therapy.

Evaluating Patient Biological Pathways Impacted by the Therapeutic Agents

The methods may be further characterized according to whether the method further comprises evaluating patient biological pathways impacted by at least one of the therapeutic agents. For example, in certain embodiments, the method further comprises evaluating patient biological pathways impacted by at least one of the therapeutic agents. In certain embodiments, the method further comprises evaluating patient biological pathways impacted by the first therapeutic agent. In certain embodiments, the method further comprises evaluating patient biological pathways impacted by the second therapeutic agent. In certain embodiments, the method further comprises evaluating patient biological pathways impacted by all therapeutic agents in the combination therapy.

Combination therapies comprising multiple therapeutic agents in order to impact two or more separate biological pathways impacting the medical disorder can provide favorable therapies for treating the medical disorder. This can result in improved efficacy and/or reduce the risk of the patient developing resistance to the treatment over time. Accordingly, in certain embodiments, the method comprises selecting a first therapeutic agent that acts on a first biological pathway impacting the medical disorder, and selecting a second therapeutic agent that acts on a second biological pathway impacting the medical disorder. In certain other embodiments, the method comprises selecting the identity of at least one therapeutic agent in the combination therapy so that the combination therapy impacts at least two different biological pathways in the patient in order to improve the therapeutic benefit of the combination. In certain other embodiments, the method comprises selecting the identity of each therapeutic agent in the combination therapy so that the combination therapy impacts at least two different biological pathways in the patient in order to improve the therapeutic benefit of the combination.

In certain embodiments, the method further comprises selecting a dosage amount for at least one therapeutic agent in the combination therapy so that the combination therapy impacts at least two different biological pathways in the patient in order to improve the therapeutic benefit of the combination. In certain embodiments, the method further comprises selecting a dosage amount for each therapeutic agent in the combination therapy so that the combination therapy impacts at least two different biological pathways in the patient in order to improve the therapeutic benefit of the combination.

Evaluating Patient Cell Types Impacted by the Therapeutic Agents

The methods may be further characterized according to whether the method further comprises evaluating patient cell types impacted by at least one of the therapeutic agents. For example, in certain embodiments, the method further comprises evaluating patient cell types impacted by at least one of the therapeutic agents. In certain embodiments, the method further comprises evaluating patient cell types impacted by the first therapeutic agent. In certain embodiments, the method further comprises evaluating patient cell types impacted by the second therapeutic agent. In certain embodiments, the method further comprises evaluating patient cell types impacted by all therapeutic agents in the combination therapy.

Combination therapies comprising multiple therapeutic agents in order to impact two or more separate cell types impacting the medical disorder can provide favorable therapies for treating the medical disorder. This can result in improved efficacy and/or reduce the risk of the patient developing resistance to the treatment over time. Accordingly, in certain embodiments, the method comprises selecting a first therapeutic agent that acts on a first cell type impacting the medical disorder, and selecting a second therapeutic agent that acts on a second cell type impacting the medical disorder. In certain other embodiments, the method comprises selecting the identity of at least one therapeutic agent in the combination therapy so that the combination therapy impacts at least two different cell types in the patient in order to improve the therapeutic benefit of the combination. In certain other embodiments, the method comprises selecting the identity of each therapeutic agent in the combination therapy so that the combination therapy impacts at least two different cell types in the patient in order to improve the therapeutic benefit of the combination.

In certain embodiments, the method further comprises selecting a dosage amount for at least one therapeutic agent in the combination therapy so that the combination therapy impacts at least two different cell types in the patient in order to improve the therapeutic benefit of the combination. In certain embodiments, the method further comprises selecting a dosage amount for each therapeutic agent in the combination therapy so that the combination therapy impacts at least two different cell types in the patient in order to improve the therapeutic benefit of the combination.

In certain embodiments, the medical disorder is a cancer, and the method comprises selecting a first therapeutic agent that acts on a cancer cell, and selecting a second therapeutic agent that acts on one or more immune-system cell types. In certain embodiments, the medical disorder is a cancer, and the method comprises selecting a first therapeutic agent that acts on one or more immune-system cell types, and selecting a second therapeutic agent that acts on a cancer cell.

Use of Biologically Constrained Neural Networks in Machine Learning

In certain embodiments, the method further comprises using a biologically constrained neural network enabled by machine learning to evaluate biological pathways that may implicate the medical disorder. Still further, in certain embodiments, a therapeutic agent is selected that targets a biological pathway identified as implicating the medical disorder.

There are many different types of machine learning models, e.g., neural networks, random forests, and elastic net. Each are applicable to the proposed technique.

The proposed neural network is constructed based on gene ontology using root ontology terms for a specified list of genes for which there is expression information. The network is pruned so that any nodes that are single input single output (SISO) are combined. The resulting network of nodes and edges then defines the neural network. The operation performed at each node is the hyperbolic-tangent of the linear weighted summation of all input tensors. Weights are determined using ADAM optimization implemented in TensorFlow. Input tensor is single drug-induced gene expression changes for both drugs and the output is synergistic efficacy or synergistic potency of the combination.

To quantify the relative contribution of each node in the neural network (with its corresponding biological process), a SHAP value can be used, which is a game theoretic metric designed to quantify the relative contributions to an outcome from non-scaled input data. The network paths with the highest SHAP values for a combination can be then investigated to understand the biological basis of the predicted synergy.

Evaluating Therapeutic Indexes

The methods may be further characterized according to whether the method further comprises evaluating the therapeutic index of at least one of the therapeutic agents. For example, in certain embodiments, the method further comprises evaluating the therapeutic index of at least one of the therapeutic agents. In certain embodiments, the method further comprises evaluating the therapeutic index of the first therapeutic agent. In certain embodiments, the method further comprises evaluating the therapeutic index of the second therapeutic agent. In certain embodiments, the method further comprises evaluating the therapeutic index of all therapeutic agents in the combination therapy.

In certain embodiments, the method further comprises selecting a dosage amount for at least one therapeutic agent in the combination therapy that improves the therapeutic index of the combination therapy. In certain embodiments, the method further comprises selecting a dosage amount for each therapeutic agent in the combination therapy that improves the therapeutic index of the combination therapy. In certain embodiments, the method further comprises selecting the identity of at least one therapeutic agent in the combination therapy in order to improve the therapeutic index of the combination therapy. In certain embodiments, the method further comprises selecting the identity of each therapeutic agent in the combination therapy in order to improve the therapeutic index of the combination therapy.

Evaluating Aqueous Solubility

The methods may be further characterized according to whether the method further comprises evaluating the aqueous solubility of at least one of the therapeutic agents. For example, in certain embodiments, the method further comprises evaluating the aqueous solubility of at least one of the therapeutic agents. In certain embodiments, the method further comprises evaluating the aqueous solubility of the first therapeutic agent. In certain embodiments, the method further comprises evaluating the aqueous solubility of the second therapeutic agent. In certain embodiments, the method further comprises evaluating the aqueous solubility of all therapeutic agents in the combination therapy.

In certain embodiments, the method further comprises selecting the identity of at least one therapeutic agent in the combination therapy in order to improve the aqueous solubility of the combination therapy. In certain embodiments, the method further comprises selecting the identity of each therapeutic agent in the combination therapy in order to improve the aqueous solubility of the combination therapy.

In certain embodiments, the method further comprises selecting a dosage amount for at least one therapeutic agent in the combination therapy that improves the aqueous solubility of the combination therapy. In certain embodiments, the method further comprises selecting a dosage amount for each therapeutic agent in the combination therapy that improves the aqueous solubility of the combination therapy.

Analyzing Biological Samples from a Patient

The methods may be further characterized according to whether the method further comprises analyzing a biological sample from a patient suspected of suffering from the medical disorder. For example, in certain embodiments, the method further comprises analyzing a biological sample from a patient suspected of suffering from the medical disorder. In certain embodiments, the biological sample is a biopsy of a tumor. In certain embodiments, the biological sample is a bodily fluid, such as saliva, urine, or blood. In certain embodiment, analyzing a biological sample from a patient comprises analyzing a tumor sample for one or more mutations.

In certain embodiments, the method further comprises selecting the identity of at least one therapeutic agent in the combination therapy based on a feature of a biological sample obtained from a patient suspected of suffering from the medical disorder. In certain embodiments, the method further comprises selecting the identity of each therapeutic agent in the combination therapy based on a feature of a biological sample obtained from a patient suspected of suffering from the medical disorder.

In certain embodiments, the method further comprises selecting a dosage amount for at least one therapeutic agent in the combination therapy based on a feature of a biological sample obtained from a patient suspected of suffering from the medical disorder. In certain embodiments, the method further comprises selecting a dosage amount for each therapeutic agent in the combination therapy based on a feature of a biological sample obtained from a patient suspected of suffering from the medical disorder. In certain embodiments, the feature is a cancer mutation.

Evaluating Oxidation State of a Biological Pathway Impacting the Medical Disorder The methods may be further characterized according to whether the method further comprises evaluating the oxidation state of a biological pathway impacting the medical disorder. For example, in certain embodiments, the method further comprises evaluating the oxidation state of a biological pathway impacting the medical disorder.

In certain embodiments, the method further comprises selecting the identity of at least one therapeutic agent in the combination therapy to impact the oxidation state of a biological pathway impacting the medical disorder. In certain embodiments, the method further comprises selecting the identity of each therapeutic agent in the combination therapy to impact the oxidation state of a biological pathway impacting the medical disorder.

In certain embodiments, the method further comprises selecting a dosage amount for at least one therapeutic agent in the combination therapy to impact the oxidation state of a biological pathway impacting the medical disorder. In certain embodiments, the method further comprises selecting a dosage amount for each therapeutic agent in the combination therapy to impact the oxidation state of a biological pathway impacting the medical disorder.

Evaluating Functional State of a Biological Pathway Impacting the Medical Disorder The methods may be further characterized according to whether the method further comprises evaluating a functional state of a biological pathway impacting the medical disorder. For example, in certain embodiments, the method further comprises evaluating a functional state of a biological pathway impacting the medical disorder.

In certain embodiments, the method further comprises selecting the identity of at least one therapeutic agent in the combination therapy to impact a functional state of a biological pathway impacting the medical disorder. In certain embodiments, the method further comprises selecting the identity of each therapeutic agent in the combination therapy to impact a functional state of a biological pathway impacting the medical disorder.

In certain embodiments, the method further comprises selecting a dosage amount for at least one therapeutic agent in the combination therapy to impact a functional state of a biological pathway impacting the medical disorder. In certain embodiments, the method further comprises selecting a dosage amount for each therapeutic agent in the combination therapy to impact a functional state of a biological pathway impacting the medical disorder.

Improving Therapeutic Benefit Towards the Medical Disorder

The methods may be further characterized according to whether the method further comprises selecting a dosage amount for at least one therapeutic agent and/or altering the identity of at least one therapeutic agent in the combination therapy, in order to improve the therapeutic benefit towards the medical disorder. For example, in certain embodiments, the method further comprises (i) selecting a dosage amount for at least one therapeutic agent in the combination that improves the therapeutic benefit towards the medical disorder or (ii) altering the identity of at least one therapeutic agent in the combination therapy to improve the therapeutic benefit towards the medical disorder.

In certain embodiments, the method further comprises selecting a dosage amount for at least one therapeutic agent in the combination that improves the therapeutic benefit towards the medical disorder. In certain embodiments, the method further comprises altering the identity of at least one therapeutic agent in the combination therapy to improve the therapeutic benefit towards the medical disorder. In certain embodiments, the method further comprises (i) selecting a dosage amount for at least one therapeutic agent in the combination that improves the therapeutic benefit towards the medical disorder, and (ii) altering the identity of at least one therapeutic agent in the combination therapy to improve the therapeutic benefit towards the medical disorder.

In certain embodiments, the method further comprises (i) selecting a dosage amount for at each therapeutic agent in the combination that improves the therapeutic benefit towards the medical disorder or (ii) altering the identity of each therapeutic agent in the combination therapy to improve the therapeutic benefit towards the medical disorder. In certain embodiments, the method further comprises selecting a dosage amount for each therapeutic agent in the combination that improves the therapeutic benefit towards the medical disorder. In certain embodiments, the method further comprises altering the identity of each therapeutic agent in the combination therapy to improve the therapeutic benefit towards the medical disorder. In certain embodiments, the method further comprises (i) selecting a dosage amount for each therapeutic agent in the combination that improves the therapeutic benefit towards the medical disorder, and (ii) altering the identity of each therapeutic agent in the combination therapy to improve the therapeutic benefit towards the medical disorder.

In certain embodiments, a greater improvement in efficacy towards the medical disorder between (i) the combination and (ii) the most efficacious single therapeutic agent in the combination indicates greater therapeutic benefit.

In certain embodiments, a greater improvement in potency towards the medical disorder for the first therapeutic agent between when (i) the first therapeutic agent is used alone and (ii) the first therapeutic agent is used in combination with the second therapeutic agent indicates greater therapeutic benefit.

In certain embodiments, a greater improvement in potency towards the medical disorder for the second therapeutic agent between when (i) the second therapeutic agent is used alone and (ii) the second therapeutic agent is used in combination with the first therapeutic agent indicates greater therapeutic benefit.

Medical Disorder

The methods may be further characterized according to the medical disorder. For example, in certain embodiments, the medical disorder is a hyperproliferative disorder, a cardiovascular disorder, an immunological and/or inflammatory disorder, a bacterial infection, a viral infection, or pain. In certain embodiments, the medical disorder is cancer.

In certain embodiments, the medical disorder is a cancer that is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

Additional Considerations

The methods may be further characterized according to the number of therapeutic agents in the combination therapy. For example, in certain embodiments, the combination therapy contains only two therapeutic agents that provide a therapeutic effect against the medical disorder. In certain embodiments, the combination therapy contains three therapeutic agents that provide a therapeutic effect against the medical disorder. In certain embodiments, the combination therapy contains at least three therapeutic agents that provide a therapeutic effect against the medical disorder. In certain embodiments, the combination therapy contains more than three therapeutic agents that provide a therapeutic effect against the medical disorder.

Exemplary More Specific Embodiments

The invention may be further exemplified by the following more specific exemplary embodiments.

In an exemplary more specific embodiment, the invention provides a method for evaluating the therapeutic benefit provided by a combination therapy comprising a first therapeutic agent and a second therapeutic agent, the method comprising determining a therapeutic effect ($E_d$) towards the medical disorder for the combination therapy, at a given concentration of first therapeutic agent and second therapeutic agent, using Equation 1:

$$E_d = \frac{C_1^{h_1} C_2^{h_2} E_0 + d_1^{h_1} C_2^{h_2} E_1 + C_1^{h_1} d_2^{h_2} E_2 + (\alpha_2 d_1)^{h_1} d_2^{h_2} E_3}{C_1^{h_1} C_2^{h_2} + d_1^{h_1} C_2^{h_2} + C_1^{h_1} d_2^{h_2} + (\alpha_2 d_1)^{h_1} d_2^{h_2}} \quad \text{(Equation 1)}$$

wherein:
$C_1$ is the concentration of the first therapeutic agent required to achieve 50% of the maximum efficacy of the combination therapy towards the medical disorder;
$C_2$ is the concentration of the second therapeutic agent required to achieve 50% of the maximum efficacy of the combination therapy towards the medical disorder;
$h_1$ is the Hill coefficient for the dose-response curve of the first therapeutic agent when the first therapeutic agent is used alone;
$h_2$ is the Hill coefficient for the dose-response curve of the second therapeutic agent when the second therapeutic agent is used alone;
$d_1$ is concentration of the first therapeutic agent;
$d_2$ is concentration of the second therapeutic agent;
$E_0$ is the basal effect (i.e. the efficacy when neither the first nor second therapeutic agent is used to treat the medical disorder);
$E_1$ is the maximum efficacy towards the medical disorder of the first therapeutic agent when the first therapeutic agent is used alone;
$E_2$ is the maximum efficacy towards the medical disorder of the second therapeutic agent when the second therapeutic agent is used alone;
$E_3$ is the maximum efficacy towards the medical disorder of the combination therapy; and
$\alpha_2$ is the fold-change in the concentration of the first therapeutic agent required to achieve 50% of the maximum efficacy towards the medical disorder of the combination therapy compared to when the first therapeutic agent is used alone.

In another exemplary more specific embodiment, the invention provides a method for evaluating the therapeutic benefit provided by a combination therapy comprising a first therapeutic agent and a second therapeutic agent, the method comprising determining a therapeutic effect ($E_d$) towards the medical disorder for the combination therapy, at a given concentration of first therapeutic agent and second therapeutic agent, using Equation 2:

$h_1$ is the Hill coefficient for the dose-response curve of the first therapeutic agent when the first therapeutic agent is used alone;
$h_2$ is the Hill coefficient for the dose-response curve of the second therapeutic agent when the second therapeutic agent is used alone;
$d_1$ is concentration of the first therapeutic agent;
$d_2$ is concentration of the second therapeutic agent;
$E_0$ is the basal effect (i.e. the efficacy when neither the first nor second therapeutic agent is used to treat the medical disorder);
$E_1$ is the maximum efficacy towards the medical disorder of the first therapeutic agent when the first therapeutic agent is used alone;
$E_2$ is the maximum efficacy towards the medical disorder of the second therapeutic agent when the second therapeutic agent is used alone;
$E_3$ is the maximum efficacy towards the medical disorder of the combination therapy;
$\alpha_1$ is the fold-change in the concentration of the second therapeutic agent required to achieve 50% of the maximum efficacy towards the medical disorder of the combination therapy compared to when the second therapeutic agent is used alone;
$\alpha_2$ is the fold-change in the concentration of the first therapeutic agent required to achieve 50% of the maximum efficacy towards the medical disorder of the combination therapy compared to when the first therapeutic agent is used alone;
$r_1$ is the rate of transition for the first therapeutic agent from the unaffected state to the affected state;
$r_{-1}$ is $r_1 * C_1^{h_1}$;
$r_2$ is the rate of transition for the second therapeutic agent from the unaffected state to the affected state; and
$r_{-2}$ is $r_2 * C_2^{h_2}$.

The foregoing exemplary more specific embodiments may be further characterized according to features described herein. For example, in certain embodiments, the method may be further characterized according to the methods employed in calculating the therapeutic effect (Ed). For instance, in certain embodiments, a curve fitting algorithm is used to calculate the therapeutic effect (Ed). In certain embodiments, the curve fitting algorithm is a Bayesian fitting algorithm. In certain embodiments, the curve fitting algorithm is a Bayesian fitting algorithm using a particle swarm optimizer to seed priors for a Markov chain Monte Carlo optimization. In certain embodiments, the curve fitting algorithm comprises use of a neural network. The method may be further characterized according to the methods of displaying the therapeutic effect (Ed). For instance, in cer- $$E_d = [E_0 E_1 E_2 E_3] \cdot \begin{bmatrix} -(r_1 d_1^{h_1} + r_2 d_2^{h_2}) & r_{-1} & r_{-2} & 0 \\ r_1 d_1^{h_1} & -(r_{-1} + r_2 (\alpha_1 d_2)^{h_2}) & 0 & r_{-2} \\ r_2 d_2^{h_2} & 0 & -(r_1 (\alpha_2 d_1)^{h_1} + r_{-2}) & r_{-1} \\ 1 & 1 & 1 & 1 \end{bmatrix}^{-1} \cdot \begin{bmatrix} 0 \\ 0 \\ 0 \\ 1 \end{bmatrix} \quad \text{(Equation 2)}$$

wherein:
$C_1$ is the concentration of the first therapeutic agent required to achieve 50% of the maximum efficacy of the combination therapy towards the medical disorder;
$C_2$ is the concentration of the second therapeutic agent required to achieve 50% of the maximum efficacy of the combination therapy towards the medical disorder;

tain embodiments, the therapeutic effect (Ed) is displayed graphically according to the determined therapeutic effect (Ed) across different doses for the first therapeutic agent. In certain embodiments, the therapeutic effect (Ed) is displayed graphically according to the determined therapeutic effect (Ed) across a dosage range for the first therapeutic agent. In certain embodiments, the therapeutic effect (Ed) is displayed graphically according to the determined therapeutic effect (Ed) across different doses for the second therapeutic agent. In certain embodiments, the therapeutic effect (Ed) is displayed graphically according to the determined therapeutic effect (Ed) across a dosage range for the second therapeutic agent.

EXAMPLES

The invention now being generally described, will be more readily understood by reference to the following examples, which are included merely for purposes of illustration of certain aspects and embodiments of the present invention, and are not intended to limit the invention.

Example 1

Method for Evaluating Therapeutic Benefit

The dose-effect relationship of a single drug is traditionally quantified by the Hill equation, which contains parameters describing efficacy ($E_{max}$) and potency ($EC_{50}$) of a dose-response curve. The Hill equation is derived from a phenomenological 2-state model of drug effect.

To characterize the dose-effect relationship for drug combinations, a 4-state model was created to derive a 2D generalization of the Hill equation, using principles of mass action kinetics. This equation parameterizes a dose-response surface, which is a two-dimensional extension of a 1D dose-response curve. In this equation, the changes in the efficacy and potency resulting from the combination are quantified by parameters for synergistic efficacy, denoted by $\beta$, and synergistic potency, denoted by $\alpha$. These parameters govern the shape of the dose-response surface and can capture complex patterns in experimental data. The equation takes the form of Equation 1 when therapeutic agents in the combination therapy obey detailed balance.

$$E_d = \frac{C_1^{h_1} C_2^{h_2} E_0 + d_1^{h_1} C_2^{h_2} E_1 + C_1^{h_1} d_2^{h_2} E_2 + (\alpha_2 d_1)^{h_1} d_2^{h_2} E_3}{C_1^{h_1} C_2^{h_2} + d_1^{h_1} C_2^{h_2} + C_1^{h_1} d_2^{h_2} + (\alpha_2 d_1)^{h_1} d_2^{h_2}} \quad \text{(Equation 1)}$$

wherein:
$E_d$ is therapeutic effect towards the medical disorder for the combination therapy, at a given concentration of first therapeutic agent and second therapeutic agent;
$C_1$ is the concentration of the first therapeutic agent required to achieve 50% of the maximum efficacy of the combination therapy towards the medical disorder;
$C_2$ is the concentration of the second therapeutic agent required to achieve 50% of the maximum efficacy of the combination therapy towards the medical disorder;
$h_1$ is the Hill coefficient for the dose-response curve of the first therapeutic agent when the first therapeutic agent is used alone;
$h_2$ is the Hill coefficient for the dose-response curve of the second therapeutic agent when the second therapeutic agent is used alone;
$d_1$ is concentration of the first therapeutic agent;
$d_2$ is concentration of the second therapeutic agent;
$E_0$ is the basal effect (i.e. the efficacy when neither the first nor second therapeutic agent is used to treat the medical disorder);
$E_1$ is the maximum efficacy towards the medical disorder of the first therapeutic agent when the first therapeutic agent is used alone;
$E_2$ is the maximum efficacy towards the medical disorder of the second therapeutic agent when the second therapeutic agent is used alone;
$E_3$ is the maximum efficacy towards the medical disorder of the combination therapy; and
$\alpha_2$ is the fold-change in the concentration of the first therapeutic agent required to achieve 50% of the maximum efficacy towards the medical disorder of the combination therapy compared to when the first therapeutic agent is used alone.

The equation takes the form of Equation 2 when therapeutic agents in the combination therapy do not obey detailed balance.

$$E_d = [E_0 E_1 E_2 E_3] \cdot \begin{bmatrix} -(r_1 d_1^{h_1} + r_2 d_2^{h_2}) & r_{-1} & r_{-2} & 0 \\ r_1 d_1^{h_1} & -(r_{-1} + r_2(\alpha_1 d_2)^{h_2}) & 0 & r_{-2} \\ r_2 d_2^{h_2} & 0 & -(r_1(\alpha_2 d_1)^{h_1} + r_{-2}) & r_{-1} \\ 1 & 1 & 1 & 1 \end{bmatrix}^{-1} \begin{bmatrix} 0 \\ 0 \\ 0 \\ 1 \end{bmatrix} \quad \text{(Equation 2)}$$

wherein:
$C_1$ is the concentration of the first therapeutic agent required to achieve 50% of the maximum efficacy of the combination therapy towards the medical disorder;
$C_2$ is the concentration of the second therapeutic agent required to achieve 50% of the maximum efficacy of the combination therapy towards the medical disorder;
$h_1$ is the Hill coefficient for the dose-response curve of the first therapeutic agent when the first therapeutic agent is used alone;
$h_2$ is the Hill coefficient for the dose-response curve of the second therapeutic agent when the second therapeutic agent is used alone;
$d_1$ is concentration of the first therapeutic agent;
$d_2$ is concentration of the second therapeutic agent;
$E_0$ is the basal effect (i.e. the efficacy when neither the first nor second therapeutic agent is used to treat the medical disorder);
$E_1$ is the maximum efficacy towards the medical disorder of the first therapeutic agent when the first therapeutic agent is used alone;
$E_2$ is the maximum efficacy towards the medical disorder of the second therapeutic agent when the second therapeutic agent is used alone;
$E_3$ is the maximum efficacy towards the medical disorder of the combination therapy;
$\alpha_1$ is the fold-change in the concentration of the second therapeutic agent required to achieve 50% of the maximum efficacy towards the medical disorder of the combination therapy compared to when the second therapeutic agent is used alone;

$\alpha_2$ is the fold-change in the concentration of the first therapeutic agent required to achieve 50% of the maximum efficacy towards the medical disorder of the combination therapy compared to when the first therapeutic agent is used alone;

$r_1$ is the rate of transition for the first therapeutic agent from the unaffected state to the affected state;

$r_{-1}$ is $r_1 * C_1^{h1}$;

$r_2$ is the rate of transition for the second therapeutic agent from the unaffected state to the affected state; and $r_{-2}$ is $r_2 * C_2^{h2}$.

The parameter β is defined as the percent increase in a drug combination's effect beyond the most efficacious single drug. For instance, in the case of synergistic efficacy (β>0), the effect at the maximum concentration of both drugs ($E_3$) exceeds the maximum effect of either drug alone ($E_1$ or $E_2$) (See FIG. 1C, quadrants I and II). For antagonistic efficacy (β<0) (see FIG. 1C, quadrants III and IV), at least one or both drugs are more efficacious as single agents than in combination The parameter α quantifies how the effective dose of one drug is altered by the presence of the other. In the case of synergistic potency (α>1), the $EC_{50}$ (denoted C in FIG. 1B) decreases because of the addition of the other drug (see FIG. 1C, quadrants I and IV), corresponding to an increase in potency. In the case of antagonistic potency (0≤α<1), the $EC_{50}$ of the drug increases as a result of the other drug (see FIG. 1C, quadrants II and III), corresponding to a decrease in potency. Since each drug can modulate the effective dose of the other independently, Equations 1 and 2 contains two α values (α1 and α2) (FIG. 1-S1B, bottom and right edges of surface). This separation of α values makes it possible for a given drug combination to have synergism of potency in one direction (α1>1), and antagonism of potency in the other (α2<1), or vice versa (see FIG. 1-S1C for example surfaces).

Both parameters for synergy of efficacy (β) and synergy of potency (α) correspond to geometric transformations of the dose-response surface, analogous to the parameters for efficacy ($E_{max}$) and potency ($EC_{50}$) that transform the single-drug dose-response curve in classic pharmacology.

In summary, Equations 1 and 2 enable a formalism, termed MuSyC, in which synergistic efficacy and synergistic potency are orthogonal and quantified by the parameters and α, respectively.

MuSyC Quantifies Synergy of Potency and Efficacy in a Drug Combination Screen

MuSyC was applied to evaluate the synergistic potency and efficacy of a 64-drug panel (see Table 1 for drugs, drug classes, nominal targets, and tested concentration ranges) in combination with osimertinib, a mutant EGFR-tyrosine kinase inhibitor recently approved for first-line treatment of EGFR-mutant NSCLC. The selected drugs span a diverse array of cellular targets that can be broadly grouped into four categories: kinases, receptors and channels, epigenetic regulators, and mitotic checkpoints, each with several subcategories. The combinations were tested in PC9 cells, a canonical model of EGFR-mutant NSCLC using a high-throughput, in vitro, drug-screening assay (FIG. 2A).

TABLE 1

Annotation of anti-cancer drugs used in NSCLC and BRAF-mutant melanoma screens with nominal target and target class.

| Class | Subclass | Drug | Tested Range | Nominal Target |
|---|---|---|---|---|
| NSCLC | | | | |
| Epigentic Regulators | BET | jq1 | 4.0 uM-0.1 nM, 0 nM | BET bromo-domain |
| | HDACi | abexinostat | 0.3 uM-0.8 nM, 0 nM | HDAC |
| | | entinostat | 1.0 uM-2.6 nM, 0 nM | HDAC |
| | | givinostat | 10.0 uM-41.1 nM, 0 nM | HDAC |
| | | m344 | 1.0 uM-2.6 nM, 0 nM | HDAC |
| | | mocetinostat | 0.3 uM-0.8 nM, 0 nM | HDAC |
| | | panobinostat | 0.4 uM-0.0 nM, 0 nM | HDAC |
| | | pracinostat | 10.0 uM-41.1 nM, 0 nM | HDAC |
| | | quisnostat | 1.0 uM-2.6 nM, 0 nM | HDAC |
| | TF | bazedoxifene | 10.0 uM-41.1 nM, 0 nM | ER |
| | | verteporfin | 10.0 uM-41.1 nM, 0 nM | YAP |
| Kinases | ALK | ceritinib | 4.0 uM-0.1 nM, 0 nM | ALK/IGF1R |
| | | ensartinib | 4.0 uM-0.1 nM, 0 nM | ALK |
| | AURK/CDKs | bml259 | 1.0 uM-2.6 nM, 0 nM | CDK |
| | | zm447439 | 4.0 uM-0.1 nM, 0 nM | AURK |
| | MAPK/PI3K | dactolisib | 4.0 uM-0.1 nM, 0 nM | PI3K/mTOR |
| | | ly294002 | 10.0 uM-41.1 nM, 0 nM | PI3K |
| | | rapamycin | 0.3 uM-0.8 nM, 0 nM | mTOR |
| | | sb253226 | 10.0 uM-41.1 nM, 0 nM | p38 |
| | | tak632 | 4.0 uM-0.1 nM, 0 nM | RAF |
| | | trametinib | 0.3 uM-0.8 nM, 0 nM | MEK |
| | | u0126 | 10.0 uM-41.1 nM, 0 nM | MEK |
| | | ulixertinib | 4.0 uM-0.1 nM, 0 nM | ERK |
| | SFK | bosutinib | 10.0 uM-41.1 nM, 0 nM | Bcr-ABL/SFK |
| | | dasatinib | 1.0 uM-3.9 nM, 0 nM | SFK |
| | | pp2 | 10.0 uM-41.1 nM, 0 nM | SFK |
| | | quercetin | 10.0 uM-41.1 nM, 0 nM | SFK |
| Mitotic Checkpoint | DNA Syn/Dam | carmastine | 10.0 uM-41.1 nM, 0 nM | DNA |
| | | methotrexate | 4.0 uM-0.1 nM, 0 nM | DHFR |
| | | olaparib | 20.0 uM-0.3 nM, 0 nM | PARP |
| | Protein Syn/Stab | carfilzomib | 4.0 uM-0.1 nM, 0 nM | Proteasome |
| | | harringtonine | 10.0 uM-41.1 nM, 0 nM | Ribosomes |
| | | mg132 | 4.0 uM-0.1 nM, 0 nM | Proteasome |
| | | tanespimycin | 4.0 uM-0.1 nM, 0 nM | HSP90 |

TABLE 1-continued

Annotation of anti-cancer drugs used in NSCLC and BRAF-mutant melanoma screens with nominal target and target class.

| Class | Subclass | Drug | Tested Range | Nominal Target |
|---|---|---|---|---|
| | Tubulin | cephalomannine | 10.0 uM-41.1 nM, 0 nM | Microtubules |
| | | docetaxel | 0.3 uM-0.8 nM, 0 nM | Microtubules |
| | | vindesine | 0.3 uM-0.8 nM, 0 nM | Microtubules |
| | | vinorelbinetartrate | 10.0 uM-41.1 nM, 0 nM | Microtubules |
| Receptors & Channels | Channels | amiodarone | 10.0 uM-41.1 nM, 0 nM | NA Channels |
| | | bendroflume-thiazide | 1.0 uM-2.6 nM, 0 nM | CI Channel |
| | | cabozantinib | 4.0 uM-0.1 nM, 0 nM | C-Met/Axl/Ret |
| | | dronedarone | 10.0 uM-41.1 nM, 0 nM | NA Channels |
| | | invacaftor | 10.0 uM-41.1 nM, 0 nM | CFTR |
| | | nateglinide | 1.0 uM-2.6 nM, 0 nM | ATP-dependent K channels |
| | GPCRs | acetylcysteine | 10.0 uM-41.1 nM, 0 nM | Glutamate receptor |
| | | aprepitant | 10.0 uM-41.1 nM, 0 nM | Neuromedin receptor |
| | | beclomethasonedipropionate | 1.0 uM-2.6 nM, 0 nM | Glucocorticoid receptor |
| | | loratadine | 10.0 uM-41.1 nM, 0 nM | Histamine H1-receptors |
| | | naftopidil | 10.0 uM-41.1 nM, 0 nM | B1-adrenergic receptor |
| | | nebivolol | 10.0 uM-41.1 nM, 0 nM | B1 receptor |
| | | sp600125 | 10.0 uM-41.1 nM, 0 nM | JNK |
| | | thioridazine | 10.0 uM-41.1 nM, 0 nM | Adrenergic receptor |
| | MAPK-RTKIs | afatinib | 4.0 uM-0.1 nM, 0 nM | EGFR/HER2 |
| | | ag 879 | 1.0 uM-2.6 nM, 0 nM | HER2/RAF-1 |
| | | gefitinib | 4.0 uM-0.1 nM, 0 nM | EGER |
| | | gsk1751853a | 10.0 uM-41.1 nM, 0 nM | IGF1R/INSR |
| | | gsk994854a | 10.0 uM-41.1 nM, 0 nM | IGF1R/INSR |
| | | gw458787a | 10.0 uM-41.1 nM, 0 nM | EGFR/ERBB4 |
| | | gw644007x | 10.0 uM-41.1 nM, 0 nM | Ret |
| | | gw694590a | 10.0 uM-41.1 nM, 0 nM | TIE2 |
| | | gw770249x | 10.0 uM-41.1 nM, 0 nM | FLT3 |
| | | linsitinib | 5.0 uM-19.5 nM, 0 nM | IGF1R |
| | | ponatinib | 4.0 uM-0.1 nM, 0 nM | FGFR |
| | | tyrphostinag370 | 10.0 uM-41.1 nM, 0 nM | PDGFRbeta |
| BRAF-Mutant Melanoma | | | | |
| Kinases | MAPK/PI3K | dabrafenib | 0.4 uM-0.39 nM, 0 nM | BRAFV600 |
| | | plx4720 | 8.0 uM-7.8 nM, 0 nM | BRAFV600E & CRAF1 |
| | | raf265 | 1.0 uM-3.9 nM, 0 nM | CRAF, BRAF, & BRAFV600E |
| | | vemurafenib | 8.0 uM-7.8 nM, 0 nM | BRAFV600 |
| | | selumetinib | 4.0 uM-61 pM, 0 nM | MEK1 |
| | | trametinib | 0.4 uM-6.1 pM, 0 nM | MEK1/2 |
| | | pd98059 | 0.4 uM-6.1 pM, 0 nM | MEK1 |
| | | cobimetinib | 0.8 uM-12 pM, 0 nM | MEK1 |

Drug effect was quantified using the drug-induced proliferation (DIP) rate, a metric that avoids temporal biases characteristic of traditional endpoint assays (see, Harris, L. A., et al. "An unbiased metric of antiproliferative drug effect in vitro," Nature Methods, 2016, vol. 13, p. 497-500). To fit the resulting dose-response surfaces, a Bayesian fitting algorithm was developed, using a particle swarm optimizer (PSO) to seed priors for a Markov chain Monte Carlo (MCMC) optimization. The algorithm also accounts for non-optimal drug dosage selection, since dose ranges that are insufficient to observe saturating effects—owing to limited solubility or potency of the drug—result in a commensurate increase in the uncertainty of MuSyC's synergy parameters.

Applying this algorithm, synergy parameters ($\alpha 1$, $\alpha 2$, and $\beta_{obs}$) were extracted from fitted surfaces for all osimertinib combinations ($\beta_{obs}$ is the observed synergistic efficacy at the maximum tested dose range).

The drug panel displays wide ranges of efficacy (E2) and potency (C) for single agents (FIG. 3-S4A). The efficacy and potency of the single agents have no relationship with the synergistic efficacy and synergistic potency when combined with osimertinib (p value>0.2) (FIG. 3-S4B), confirming MuSyC's synergy parameters are independent of single agents' dose-response curve and therefore, as expected, cannot be predicted from the single-agent, pharmacologic profiles.

Figure 2E:
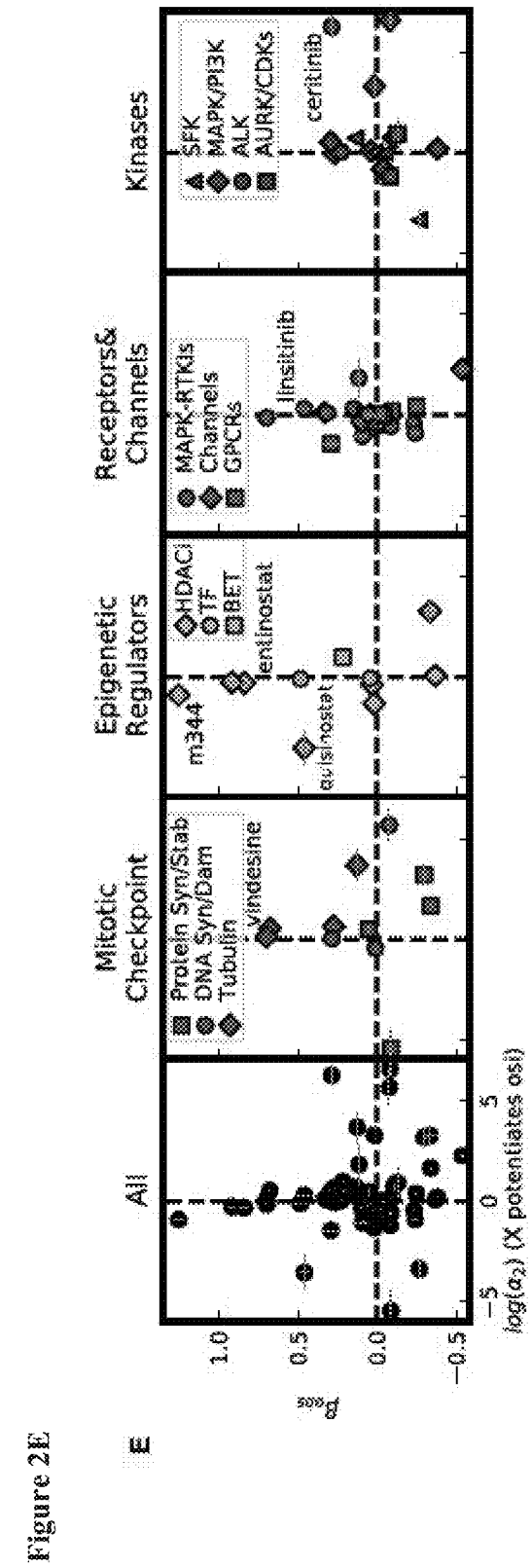
FIG. 2E illustrates drug-synergy diagrams (DSDs) for drug combinations. The vertical axis quantifies the observed synergistic efficacy ($\beta_{obs}$). The horizontal axis ($\log(\alpha 2)$) quantifies how osimertinib's potency is modulated by each drug.

Inspection of dose-response surfaces from this combination screen highlights the significance of resolving synergistic potency and efficacy. For instance, the dose-response surface for the osimertinib combination with M344 (a histone deacetylase [HDAC] inhibitor) exhibits synergistic efficacy ($\beta_{obs}$=1.25±0.03, reflecting a 125% increase in efficacy over osimertinib alone) (FIGS. 2B and 2E). However, this improved efficacy comes at the cost of potency ($\log(\alpha 2)$=−0.90±0.01) as observed in the shift in the $EC_{50}$ of osimertinib in the presence of 1 µM M344 (FIG. 2B; red to purple dotted line). In contrast, ceritinib, an ALK inhibitor with off-target effects on IGF1R increases osimertinib's potency ($\log(\alpha 2)$=6.25±0.50) (FIG. 2C; green to orange dotted line) at 4 µM (maximal tested concentration) but with inconsequential improvement of efficacy ($\beta_{obs}$=0.28 ±0.003). The shift in potency is proportional to the concentration used and would, therefore, increase at higher concentrations; however, such concentrations are not physiologically realizable because of the low potency of ceritinib in this system ($EC_{50}$=2.02 µM), highlighting the importance of interpreting synergistic potency in the context of the absolute potency.

To visualize synergy globally, drug combinations were plotted on drug-synergy diagrams (DSDs), with observed synergistic efficacy ($\beta_{obs}$) and potency on the vertical and horizontal axes, respectively (FIG. 2E). These DSDs reveal distinguishing trends between the four drug categories tested.

Figure 2F:
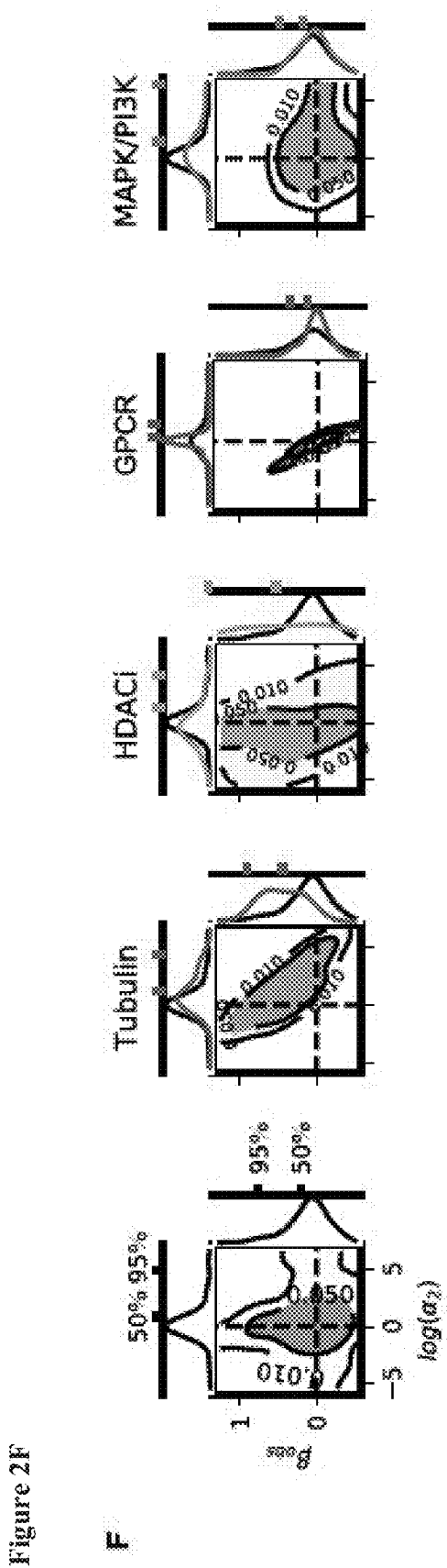
FIG. 2F depicts 2D density plots and associated marginal distributions for $\beta_{obs}$ (vertical axis) and $\alpha_2$ (horizontal axis) for all drugs (black, far left-hand plot) and selected category subclasses. Colored tick marks indicate the 50% and 95% probability density intervals for each distribution.

Within the mitotic checkpoint drugs, tubulin destabilizers (including vindesine and vinorelbine) showed an upward shift along the axis of synergistic efficacy (FIG. 2E). The marginal distribution confirmed this trend in comparison to all the drugs (FIG. 2F, blue versus black vertical distributions). Similar results were obtained for the histone deacetylase inhibitor (HDACi) subgroup within the epigenetic regulators (FIGS. 2E and 2F). As expected, limited synergistic or antagonistic efficacy was observed for drugs targeting G-protein-coupled receptors (GPCRs) (FIGS. 2E and 2F; red versus black distributions). Limited synergistic efficacy was observed when directly co-targeting kinases in the MAPK pathway, suggesting this may be an unproductive avenue in EGFR-mutant NSCLC (FIGS. 2E and 2F; purple to black comparison along vertical axis).

In summary, by quantifying synergy of potency separate from synergy of efficacy, MuSyC reveals drug-class trends, which can be used to guide subsequent screens and drug combination deployment in NSCLC.

MuSyC Validates Co-targeting RAF and MEK in BRAF-Mutant Melanoma

The NSCLC drug screen (FIG. 2) suggests combinations targeting molecules within the same signaling pathway may not be productive avenues for increasing efficacy. However, a combination used clinically in BRAF-mutant melanoma co-targets kinases BRAF and MEK in the MAPK pathway. To investigate this combination in more detail, a panel of 8 BRAFV600-mutant melanoma cell lines was screened against 16 BRAF inhibitor/MEK inhibitor (BRAFi/MEKi) combinations (see Table 1 for drug information and tested dose ranges).

Based on the mean $\beta_{obs}$ across cell lines, all 16 combinations were synergistically efficacious (FIGS. 3A and 3-S5C), indicating MuSyC would have identified this treatment strategy prospectively. In contrast, conventional methods produce ambiguous results (FIGS. 3-S6A and 3-S6B, top 3 panels in each cell line group), such that this combination strategy could have not been identified. Furthermore, MuSyC detected variations in synergistic efficacy between cell lines (FIGS. 3A and 3-S5C), underscoring its sensitivity and pointing to heterogeneous, cell-intrinsic mechanisms modulating the efficacy of combined BRAF and MEK inhibition. In particular, A2058 displayed low average synergistic efficacy, suggesting that its canonical insensitivity to BRAFi does not depend on MEK reactivation but rather on altered metabolic phenotype.

MuSyC also provides information on synergistic potency for these combinations. A clinically deployed combination (dabrafenib and trametinib) is synergistically efficacious but antagonistically potent in all cell lines except one (FIG. 3-S5), a trade-off that may be relevant in the clinic.

Together, MuSyC analyses of NSCLC and of melanoma combination screens indicate that the magnitude of a drug combination's synergistic efficacy depend upon the oncogenetic context, i.e., co-targeting within the MAPK pathway may work for mutant-BRAF melanoma but not for mutant-EGFR NSCLC.

MuSyC Reveals Whether Molecular Correlates of Insensitivity Alter Synergistic Efficacy or Potency While drug combinations are commonly identified from top-down approaches (e.g., high-throughput drug screens), others, including BRAFi/MEKi, were discovered from a bottom-up approach by investigating molecular correlates of insensitivity. However, these molecular correlates may alter either the potency or the efficacy of the primary drug (or both). MuSyC can distinguish among these possibilities, enabling an informed choice between improving either efficacy or potency. As an example, experiments were conducted to identify molecular correlates of BRAFi insensitivity between subclones of a BRAF-mutant melanoma cell line (SKMEL5) with differential sensitivity to BRAFi (FIG. 4A).

Specifically, gene expression was quantified using RNA sequencing (RNA-seq) and the top 200 differentially expressed genes (DEGs) (FDR<0.001) were identified. This gene set was significantly enriched in processes, cellular components, and molecular functions relating to metabolism (FIG. 4B), aligning with previous reports on the relationship between altered metabolism and resistance to BRAFi. The correlation was computed of the 200 DEGs' expression to BRAFi sensitivity across a 10-cell-line panel using expression data from Subramanian, A. et al. (2017). in *Cell* vol. 171, 1437-1452.e17.

Figures 4D, 4E:
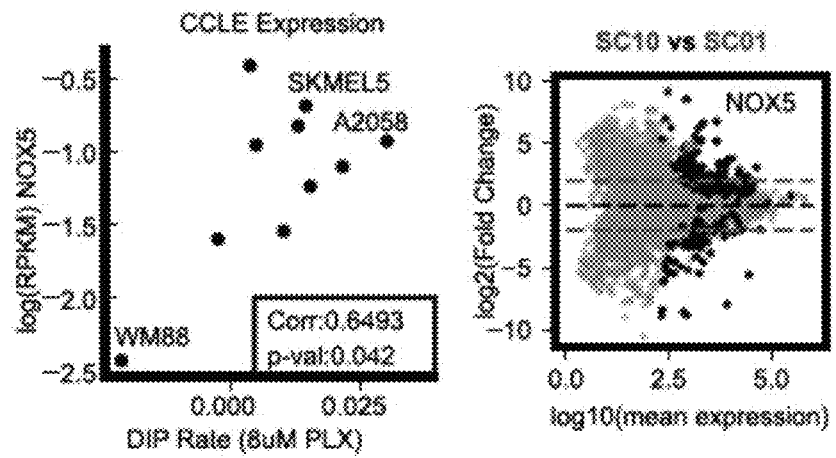
FIGS. 4D, 4E, and 4F depict data demonstrating that NOX5, a molecular correlate of insensitivity to BRAFi, is a synergistically efficacious co-target in BRAF-mutant melanoma.

NOX5 stood out as one of five genes with a significant, positive correlation with BRAFi insensitivity (Pearson r=0.65; p value=0.042) (FIGS. 4C and 4D; Table 2 for quantification of BRAFi insensitivity and Table 3 for genes correlated with BRAFi insensitivity) and was significantly up-regulated in the BRAFi-insensitive subclone (SC10) compared with the sensitive subclone (SC01) (FIG. 4E). Previously unconsidered, NOX5 is an interesting target because of its convergent regulation on metabolic and redox signaling at mitochondria, processes significantly enriched in the DEGs (FIG. 4B).

TABLE 2

BRAFi sensitivity across CCLE BRAF-mutant melanoma cell line panel.

| CCLE Cell Line | DIP Rate ($h^{-1}$) at [8 uM] PLX4270 |
|---|---|
| A2058_SKIN | 0.030 |
| A375_SKIN | 0.005 |
| SKMEL28_SKIN | 0.010 |
| SKMEL5_SKIN | 0.014 |
| WM115_SKIN | 0.013 |
| WM1799_SKIN | -0.002 |
| WM2664_SKIN | 0.003 |
| WM793_SKIN | 0.015 |
| WM88_SKIN | -0.020 |
| WM983B_SKIN | 0.021 |

TABLE 3

Differentially Expressed Genes (DEGs) between SKMEL5 subclones
SC01, SC07, SC10 whose expression significantly correlated to
BRAFi insensitivity (Pearson r) across panel of 10 cell-lines.

| Positive Correlation with BRAFi insensitivity | | | Negative Correlation with BRAFi insensitivity | | |
|---|---|---|---|---|---|
| Gene symbol | r | p-value | Gene symbol | r | p-value |
| SLC7A11 | 0.816 | 0.004 | GRIK3 | −0.743 | 0.014 |
| SLC16A7 | 0.807 | 0.005 | PRELP | −0.720 | 0.019 |
| TGFB1 | 0.666 | 0.036 | CPVL | −0.684 | 0.029 |
| NOX5 | 0.649 | 0.042 | ITGA10 | −0.659 | 0.038 |
| LXN | 0.646 | 0.044 | | | |

Figure 3A:
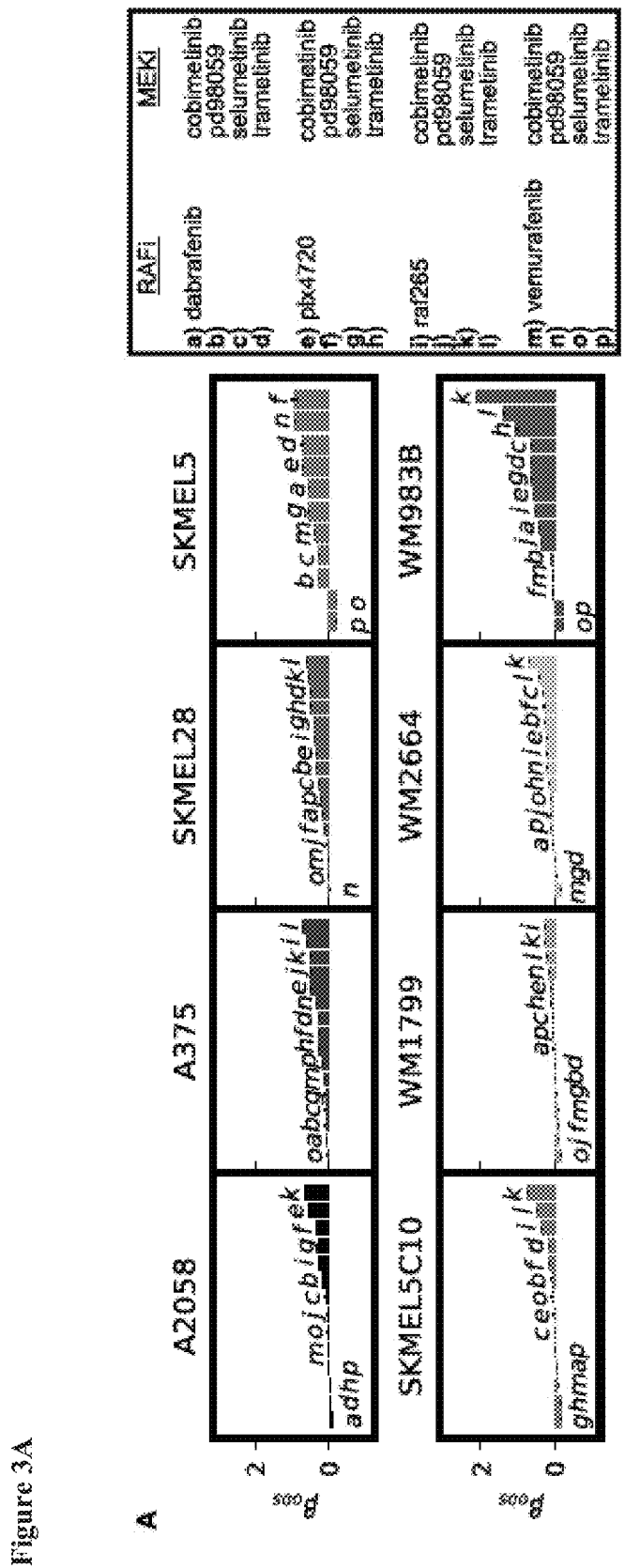
FIG. 3A depicts waterfall plots of $\beta_{obs}$ determined upon treatment of 8 BRAF-mutant melanoma cell lines (i.e., A2058, A375, etc.) with the indicated combinations of RAF and MEK inhibitors (described in the right-hand legend, e.g., combination "a" is dabrafenib and cobimetinib, combination "b" is dabrafenib and pd98059, etc.).
Figure 4F:
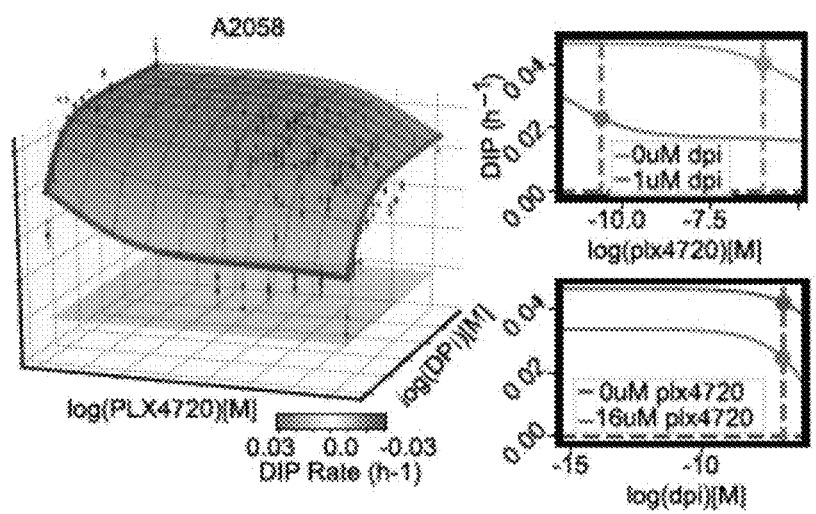

To study NOX5's contribution to the potency or efficacy of BRAFi, PLX4720 was tested in combination with a NOX5 inhibitor, DPI, in a panel of 7 melanoma cell lines selected based on differential NOX5 expression. Synergistic efficacy was found to correlate with NOX5 expression (Pearson r=0.77; p value=0.043) (FIGS. 4G and 4H); however, synergistic potency did not (Pearson r=0.01; p value=0.96) (FIGS. 4G and 4I). Of note, A2058, well known for its resistance to BRAFi, exhibited the highest NOX5 expression among the cell lines and the highest synergistic efficacy ($\beta_{obs}$=1.42 ±0.05) (FIG. 4F), which was more synergistically efficacious than all tested MEKiBRAFi combinations (FIG. 3A). See also, Meyer et al. in *Cell Systems* (2010) vol 8, pages 97-108, which is hereby incorporated by reference for all purposes.

Taken together, these results suggest co-targeting NOX5 in BRAF-mutant melanoma could lead to improved outcomes for BRAF-mutant melanoma patients with a unique metabolic program for which NOX5 is a biomarker. Furthermore, this study demonstrates the utility of MuSyC for distinguishing a molecular constituent's role in modulating the potency or efficacy of a drug.

Concluding Remarks

One goal of using synergistic drugs is to achieve more with less. Two types of synergy exist: one corresponding to how much more is achievable (synergistic efficacy) and the other to how much less is required (synergistic potency). Finding such combinations is vital for optimizing therapeutic windows, as there exists a fundamental trade-off between clinical efficacy and tolerable doses. Diseases for which single-drug efficacy is sufficient would benefit from synergistically potent combinations to drive down toxicity and/or side effects. Diseases with treatments of insufficient efficacy are in pressing need of synergistically efficacious combinations in order to improve the depth and durability of response. By stratifying synergy along distinct axes of potency and efficacy using MuSyC, informed choices can be made about this trade-off. The distinction facilitates identifying drug-class trends that can be iteratively expanded in future screens to optimize synergistic efficacy or synergistic potency, whichever is desirable for a particular disease.

In this respect, MuSyC provides a global view of the synergistic behavior of whole classes of drugs, e.g., from a high-throughput drug screen, via DSDs. In this work, MuSyC revealed a subclass of epigenetic regulators as potentially interesting targets for combination therapy in an EGFR-oncogene-addicted background. Epigenetic regulators have previously been suggested to prime NSCLC for sensitivity to EGFRi, and the HDACi entinostat in combination with erlotinib (first generation EGFR-TKI) has been shown to increase overall survival in EGFR-mutant NSCLC cases with high expression of E-cadherin. Consistent with this, entinostat was also observed to be synergistically efficacious with osimertinib ($\beta_{obs}$=0.84±0.027) in PC9 cells, an E-cadherin high-expressing cell line. As is typical of high-throughput screens, there were results of undetermined significance, including dronedarone (an anti-arrhythmic sodium channel inhibitor) and GW694590a (an anti-angiogenesis compound targeting the TIE2 receptor), which were the most antagonistic and synergistically efficacious compounds out of the receptors and channels drug classes, respectively. Further studies are needed to verify these results. Nonetheless, MuSyC provides a quantitative foundation to further investigate unsuspected combinations.

The global views provided by the MuSyC DSDs also reveal synergistic trends that vary according to disease context. For example, co-targeting the MAPK pathway in NSCLC or BRAF-mutant melanoma yields different outcomes: in the former, only synergistic potency is observed, while in the latter, synergistic efficacy, and sometimes potency, are registered. The disparity emphasizes that synergistic trends require data-driven metrics that distinguish between synergy of efficacy and potency.

MuSyC dose-response surfaces facilitate evaluating the significance that combination synergy should be assigned; that is, MuSyC's synergy parameters quantify the relative increase in efficacy or potency of the combination, with respect to single agents, and therefore, the improvements should be interpreted in the context of the absolute potency and efficacy. This information is directly conveyed in the topology of the dose-response surface. As an example, in the NSCLC screen, the combination of osimertinib with quisinostat exhibited the greatest total efficacy. However, since quisinostat is already significantly efficacious on its own, that combination ranks lower than the M344-osimertinib combination along the axis of synergistic efficacy on a DSD. Thus, DSDs are useful to rank relative increase in potency or efficacy, whereas surfaces convey the absolute efficacy and potency achieved by a combination.

MuSyC is also useful for investigating a molecular species' contribution to the potency and efficacy of a compound. Here, NOX5 activity was demonstrated to modulate the efficacy, but not the potency, of BRAFi. However, the NOX5i used, DPI, is known to have off-target effects; therefore, further evidence for the role of NOX5 in BRAFi efficacy will require extending MuSyC to studies combining drugs and gene silencing technology (e.g., RNAi or CRISPR).

To fit the dose response surface and extract synergy parameters, MuSyC utilizes a Bayesian approach combining PSO and a multi-tier MCMC walk, in order to track uncertainty in the values for synergistic potency and efficacy. The sources for this uncertainty include noise, partial dose-response curves, and data density.

While DIP rate was used as the metric of effect, MuSyC may be applied to any quantifiable phenotype whose dose response is suitable to be fit by a Hill equation. In contrast, all other synergy models surveyed impose strict constraints on the type and/or magnitude of the drug effect metric. Thus, MuSyC opens up the potential to study synergy of drug effects previously impossible to address by existing methods. Examples of metrics include immune activation, growth in 3D culture, or second messenger efflux. The flexibility is particularly critical in translating drug combinations to the clinic by using models of increasing complexity, such as organoids, which better represent the drug sensitivity of a patient. Indeed, that most clinical combinations can be explained by patient-to-patient variability is a strong rationale for translating combination screens to more complex, pre-clinical models. Subsequent work will be devoted to scaling the combination drug screening pipeline developed here to pre-clinical experimental models of increasing complexity, such as organoids.

In conclusion, MuSyC is a drug synergy framework that maintains a distinction between two intuitive types of pharmacological synergy and that may be applied to any drug effect metric. This framework allows for a richer understanding of drug interactions, with practical, translational consequences.

Figure 5:
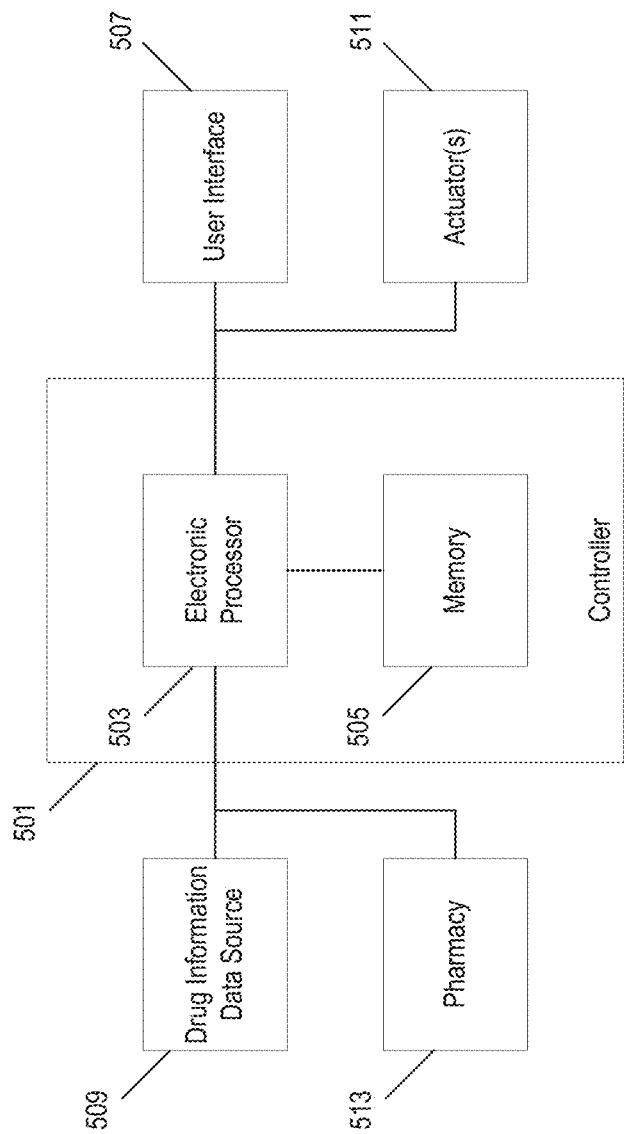
FIG. 5 is a block diagram of a system for evaluating and selecting therapeutic agents for combination therapies.

The MuSyC framework (and other methods described above) can, in some implementations, be implemented in wholly or partially automated systems. FIG. 5 illustrates one example of a system for implementing the MuSyC approach. A controller 501 includes an electronic processor 503 and a computer-readable non-transitory memory 505. The memory 505 stores data and instructions that are accessed and executed by the electronic processor 503 to provide functionality of the controller 501. The controller 501 is coupled to a user interface 507 (e.g., a keyboard, mouse, display screen, and/or touch-screen interface) to display information to a user and to receive data & control inputs from a user. In some implementations, the controller 501 and/or the user interface 507 may be provided as a desktop, laptop, or tablet computer system.

The controller 501 is also communicatively coupled to a drug information data source 509—a memory (e.g., a remote storage server) that stores information relating, for example, to the efficacy and/or potency of various different therapeutic agents. In some implementations, the controller 501 may also be coupled to one or more actuators 511 configured to automate a process for testing the therapeutic agents or for automatically administering a therapeutic agent (or combination of therapeutic agents). Similarly, in some implementations, the controller 501 may be communicatively coupled to a pharmacy computer system 513 to initiate the dispensing of a therapeutic agent or combination of therapeutic agents based on the output of the MuSyC evaluation.

Figure 6:
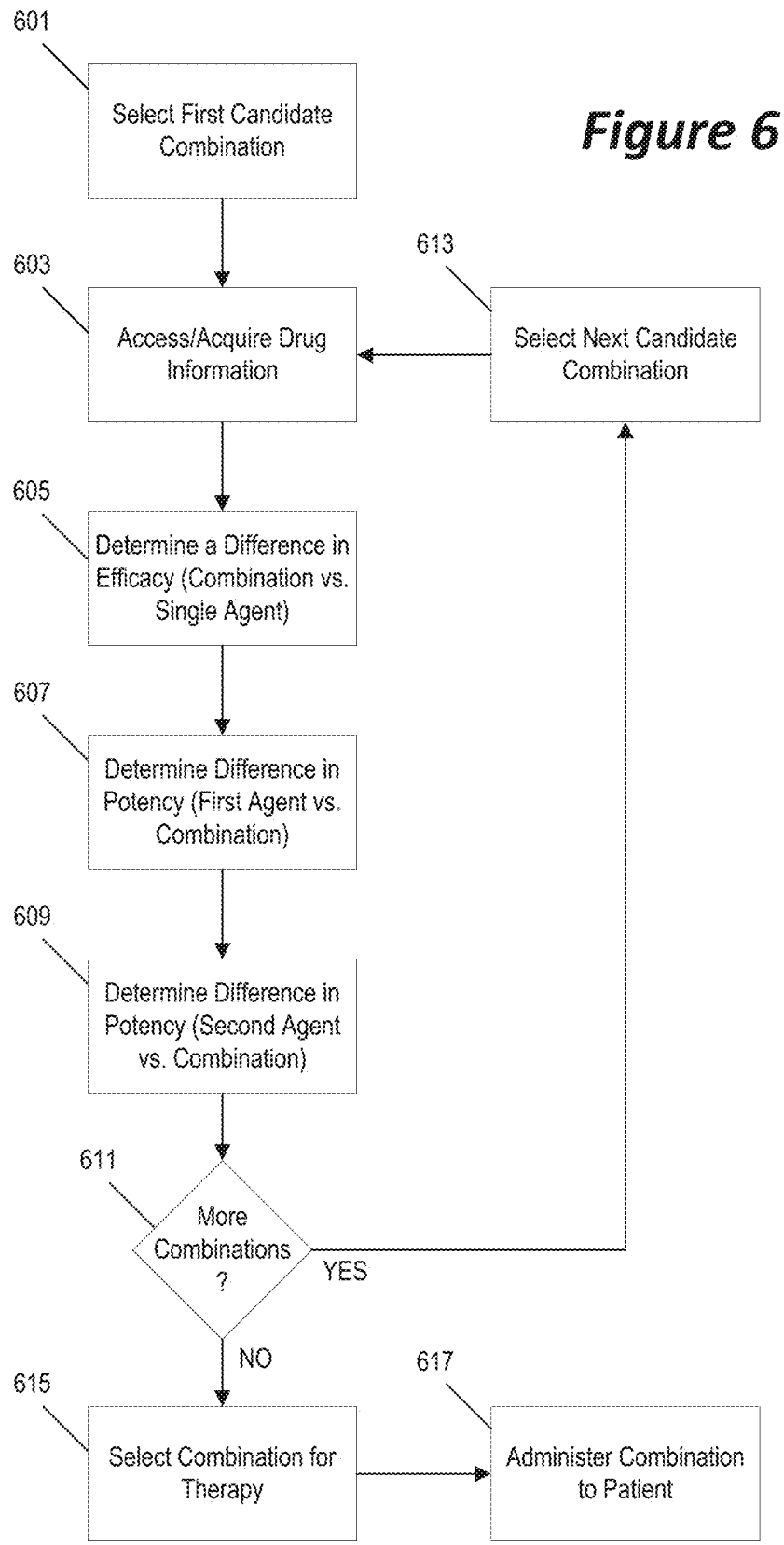
FIG. 6 is a flowchart of a method for evaluating, selecting, and administering a combination therapy using the system of FIG. 5.

FIG. 6 illustrates one example of a method for evaluating multiple different combination therapies, selecting one, and administering the selected combination therapy that may be implemented by the system of FIG. 5. The system selects a first candidate combination of a plurality of possible combinations of therapeutic agents (step 601) and acquires drug efficacy and potency information for the first candidate combination (step 603). This information can be acquired, for example, from a database of drug information or as the output of experimental analysis. Based on the acquired information for the first candidate combination, the system determines a difference in efficacy towards the medical disorder between (i) the first candidate combination and (ii) the most efficacious single therapeutic agent in the combination (step 605). The system then determines a difference in potency towards the medical disorder for the first therapeutic agent between when (i) the first therapeutic agent is used alone and (ii) the first therapeutic agent is used in combination with the second therapeutic agent (step 607). Finally, the system determines a difference in potency towards the medical disorder for the second therapeutic agent between when (i) the second therapeutic agent is used alone and (ii) the second therapeutic agent is used in combination with the first therapeutic agent (step 609). This evaluation process is repeated for each additional candidate combination (step 613) until all candidate combinations have been evaluated (step 611). After all candidate combinations have been evaluated (step 611), a particular candidate combination is selected for the therapy (step 615) based on the results of the MuSyC evaluation and the selected combination is administered to a patient (step 617).

The entire disclosure of each of the patent documents and scientific articles referred to herein is incorporated by reference for all purposes.

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

EXAMPLE 1: A method for evaluating the therapeutic benefit of a combination therapy comprising a first therapeutic agent and a second therapeutic to be used in combination to treat a medical disorder, comprising the steps of:
  (a) determining a difference in efficacy towards the medical disorder between (i) the combination and (ii) the most efficacious single therapeutic agent in the combination;
  (b) determining a difference in potency towards the medical disorder for the first therapeutic agent between when (i) the first therapeutic agent is used alone and (ii) the first therapeutic agent is used in combination with the second therapeutic agent; and
  (c) determining a difference in potency towards the medical disorder for the second therapeutic agent between when (i) the second therapeutic agent is used alone and (ii) the second therapeutic agent is used in combination with the first therapeutic agent.

EXAMPLE 2: The method of example 1, wherein step (a) comprises determining, for a plurality of different doses for each therapeutic agent in the combination, the difference in efficacy towards the medical disorder between (i) the combination and (ii) the most efficacious single therapeutic agent in the combination.

EXAMPLE 3: The method of example 1, wherein step (a) comprises determining, across a dosage range for each therapeutic agent in the combination, the difference in efficacy towards the medical disorder between (i) the combination and (ii) the most efficacious single therapeutic agent in the combination.

EXAMPLE 4: The method of any one of examples 1-3, wherein step (b) comprises determining, for a plurality of different doses of the first therapeutic agent, the difference in potency towards the medical disorder for the first therapeutic agent between when (i) the first therapeutic agent is used alone and (ii) the first therapeutic agent is used in combination with the second therapeutic agent.

EXAMPLE 5: The method of any one of examples 1-3, wherein step (b) comprises determining, across a dosage range for the first therapeutic agent, the difference in potency towards the medical disorder for the first therapeutic agent between when (i) the first therapeutic agent is used alone and (ii) the first therapeutic agent is used in combination with the second therapeutic agent.

EXAMPLE 6: The method of any one of examples 1-5, wherein step (c) comprises determining, for a plurality of different doses of the second therapeutic agent, the difference in potency towards the medical disorder for the second therapeutic agent between when (i) the second therapeutic agent is used alone and (ii) the second therapeutic agent is used in combination with the first therapeutic agent.

EXAMPLE 7: The method of any one of examples 1-5, wherein step (c) comprises determining, across a dosage range for the second therapeutic agent, the difference in potency towards the medical disorder for the second therapeutic agent between when (i) the second therapeutic agent is used alone and (ii) the second therapeutic agent is used in combination with the first therapeutic agent.

EXAMPLE 8: The method of any one of examples 1-7, wherein results from determining the difference in efficacy from step (a) are cross-referenced with results from one or both of: (i) results from determining the difference in potency towards the medical disorder for the first therapeutic agent from step (b), and (ii) results from determining the difference in potency towards the medical disorder for the second therapeutic agent from step (c).

EXAMPLE 9: The method of any one of examples 1-7, wherein results from determining the difference in efficacy towards the medical disorder from step (a) are cross-referenced with results from one or both of: (i) results from determining the difference in potency towards the medical disorder for the first therapeutic agent from step (b), and (ii) results from determining the difference in potency for the second therapeutic agent from step (c); to generate a graphical display of therapeutic effect according to the dose of first therapeutic agent and dose of second therapeutic agent.

EXAMPLE 10: The method of example 1, wherein the method comprises determining a therapeutic effect ($E_d$) towards the medical disorder for the combination therapy, at a given concentration of first therapeutic agent and second therapeutic agent, using Equation 1:

$$E_d = \frac{C_1^{h_1} C_2^{h_2} E_0 + d_1^{h_1} C_2^{h_2} E_1 + C_1^{h_1} d_2^{h_2} E_2 + (\alpha_2 d_1)^{h_1} d_2^{h_2} E_3}{C_1^{h_1} C_2^{h_2} + d_1^{h_1} C_2^{h_2} + C_1^{h_1} d_2^{h_2} + (\alpha_2 d_1)^{h_1} d_2^{h_2}} \quad \text{(Equation 1)}$$

wherein:

$C_1$ is the concentration of the first therapeutic agent required to achieve 50% of the maximum efficacy of the combination therapy towards the medical disorder;

$C_2$ is the concentration of the second therapeutic agent required to achieve 50% of the maximum efficacy of the combination therapy towards the medical disorder;

$h_1$ is the Hill coefficient for the dose-response curve of the first therapeutic agent when the first therapeutic agent is used alone;

$h_2$ is the Hill coefficient for the dose-response curve of the second therapeutic agent when the second therapeutic agent is used alone;

$d_1$ is concentration of the first therapeutic agent;

$d_2$ is concentration of the second therapeutic agent;

$E_0$ is the basal effect (i.e. the efficacy when neither the first nor second therapeutic agent is used to treat the medical disorder);

$E_1$ is the maximum efficacy towards the medical disorder of the first therapeutic agent when the first therapeutic agent is used alone;

$E_2$ is the maximum efficacy towards the medical disorder of the second therapeutic agent when the second therapeutic agent is used alone;

$E_3$ is the maximum efficacy towards the medical disorder of the combination therapy; and $\alpha_2$ is the fold-change in the concentration of the first therapeutic agent required to achieve 50% of the maximum efficacy towards the medical disorder of the combination therapy compared to when the first therapeutic agent is used alone.

EXAMPLE 11: The method of example 1, wherein the method comprises determining a therapeutic effect ($E_d$) towards the medical disorder for the combination therapy, at a given concentration of first therapeutic agent and second therapeutic agent, using Equation 2:

$$E_d = [E_0 E_1 E_2 E_3] \cdot \begin{bmatrix} -(r_1 d_1^{h_1} + r_2 d_2^{h_2}) & r_{-1} & r_{-2} & 0 \\ r_1 d_1^{h_1} & -(r_{-1} + r_2(\alpha_1 d_2)^{h_2}) & 0 & r_{-2} \\ r_2 d_2^{h_2} & 0 & -(r_1(\alpha_2 d_1)^{h_1} + r_{-2}) & r_{-1} \\ 1 & 1 & 1 & 1 \end{bmatrix}^{-1} \begin{bmatrix} 0 \\ 0 \\ 0 \\ 1 \end{bmatrix} \quad \text{(Equation 2)}$$

wherein:

$C_1$ is the concentration of the first therapeutic agent required to achieve 50% of the maximum efficacy of the combination therapy towards the medical disorder;

$C_2$ is the concentration of the second therapeutic agent required to achieve 50% of the maximum efficacy of the combination therapy towards the medical disorder;

$h_1$ is the Hill coefficient for the dose-response curve of the first therapeutic agent when the first therapeutic agent is used alone;

$h_2$ is the Hill coefficient for the dose-response curve of the second therapeutic agent when the second therapeutic agent is used alone;

$d_1$ is concentration of the first therapeutic agent;

$d_2$ is concentration of the second therapeutic agent;

$E_0$ is the basal effect (i.e. the efficacy when neither the first nor second therapeutic agent is used to treat the medical disorder);

$E_1$ is the maximum efficacy towards the medical disorder of the first therapeutic agent when the first therapeutic agent is used alone;

$E_2$ is the maximum efficacy towards the medical disorder of the second therapeutic agent when the second therapeutic agent is used alone;

$E_3$ is the maximum efficacy towards the medical disorder of the combination therapy;

$\alpha_1$ is the fold-change in the concentration of the second therapeutic agent required to achieve 50% of the maximum efficacy towards the medical disorder of the combination therapy compared to when the second therapeutic agent is used alone;

$\alpha_2$ is the fold-change in the concentration of the first therapeutic agent required to achieve 50% of the maximum efficacy towards the medical disorder of the combination therapy compared to when the first therapeutic agent is used alone;

$r_1$ is the rate of transition for the first therapeutic agent from the unaffected state to the affected state;

$r_{-1}$ is $r_1 * C_1^{h1}$;

$r_2$ is the rate of transition for the second therapeutic agent from the unaffected state to the affected state; and $r_{-2}$ is $r_2 * C_2^{h2}$.

EXAMPLE 12: The method of examples 10 or 11, wherein the therapeutic effect ($E_d$) is determined at a plurality of different doses for the first therapeutic agent.

EXAMPLE 13: The method of examples 10 or 11, wherein the therapeutic effect ($E_d$) is determined across a dosage range for the first therapeutic agent.

EXAMPLE 14: The method of any one of examples 10-13, wherein the therapeutic effect ($E_d$) is determined at a plurality of different doses for the second therapeutic agent.

EXAMPLE 15: The method of any one of examples 10-13, wherein the therapeutic effect ($E_d$) is determined across a dosage range for the second therapeutic agent.

EXAMPLE 16: The method of any one of examples 10-15, wherein a curve fitting algorithm is used to calculate the therapeutic effect ($E_d$).

EXAMPLE 17: The method of example 16, wherein the curve fitting algorithm is a Bayesian fitting algorithm.

EXAMPLE 18: The method of example 16, wherein the curve fitting algorithm is a Bayesian fitting algorithm using a particle swarm optimizer to seed priors for a Markov chain Monte Carlo optimization.

EXAMPLE 19: The method of any one of examples 10-18, wherein the therapeutic effect ($E_d$) is displayed graphically according to the determined therapeutic effect ($E_d$) across different doses for the first therapeutic agent.

EXAMPLE 20: The method of any one of examples 10-19, wherein the therapeutic effect ($E_d$) is displayed graphically according to the determined therapeutic effect ($E_d$) across different doses for the second therapeutic agent.

EXAMPLE 21: The method of any one of examples 1-20, further comprising evaluating the pharmacokinetic properties of the first therapeutic agent.

EXAMPLE 22: The method of any one of examples 1-21, further comprising evaluating the pharmacokinetic properties of the second therapeutic agent.

EXAMPLE 23: The method of any one of examples 1-20, further comprising evaluating the pharmacokinetic properties of all therapeutic agents in the combination therapy.

EXAMPLE 24: The method of any one of examples 21-23, further comprising selecting a dosage amount for at least one therapeutic agent in the combination therapy to improve the therapeutic benefit of the combination in view of the pharmacokinetic properties.

EXAMPLE 25: The method of any one of examples 21-24, further comprising selecting the identity of at least one therapeutic agent in the combination therapy in order to improve the therapeutic benefit of the combination in view of pharmacokinetic properties of the therapeutic agent.

EXAMPLE 26: The method of any one of examples 1-25, further comprising evaluating the safety profile of the first therapeutic agent.

EXAMPLE 27: The method of any one of examples 1-26, further comprising evaluating the safety profile of the second therapeutic agent.

EXAMPLE 28: The method of any one of examples 1-25, further comprising evaluating the safety profile of all therapeutic agents in the combination therapy.

EXAMPLE 29: The method of any one of examples 1-28, further comprising selecting a dosage amount for at least one therapeutic agent in the combination therapy that improves the safety profile of the combination therapy.

EXAMPLE 30: The method of any one of examples 1-29, further comprising selecting the identity of at least one therapeutic agent in the combination therapy in order to improve the safety profile of the combination therapy.

EXAMPLE 31: The method of any one of examples 1-30, further comprising evaluating the toxicity profile of the first therapeutic agent.

EXAMPLE 32: The method of any one of examples 1-31, further comprising evaluating the toxicity profile of the second therapeutic agent.

EXAMPLE 33: The method of any one of examples 1-30, further comprising evaluating the toxicity profile of all therapeutic agents in the combination therapy.

EXAMPLE 34: The method of any one of examples 1-33, further comprising selecting a dosage amount for at least one therapeutic agent in the combination therapy that improves the toxicity profile of the combination therapy.

EXAMPLE 35: The method of any one of examples 1-34, further comprising selecting the identity of at least one therapeutic agent in the combination therapy in order to improve the toxicity profile of the combination therapy.

EXAMPLE 36: The method of any one of examples 1-35, further comprising evaluating patient biological pathways impacted by the first therapeutic agent.

EXAMPLE 37: The method of any one of examples 1-36, further evaluating patient biological pathways impacted by the second therapeutic agent.

EXAMPLE 38: The method of any one of examples 1-35, further comprising evaluating patient biological pathways of all therapeutic agents in the combination therapy.

EXAMPLE 39: The method of any one of examples 1-38, further comprising selecting the identity of at least one therapeutic agent in the combination therapy so that the combination therapy impacts at least two different biological pathways in the patient in order to improve the therapeutic benefit of the combination.

EXAMPLE 40: The method of any one of examples 1-39, further comprising evaluating the therapeutic index of the first therapeutic agent.

EXAMPLE 41: The method of any one of examples 1-40, further comprising evaluating the therapeutic index of the second therapeutic agent.

EXAMPLE 42: The method of any one of examples 1-40, further comprising evaluating the therapeutic index of all therapeutic agents in the combination therapy.

EXAMPLE 43: The method of any one of examples 1-42, further comprising selecting a dosage amount for at least one therapeutic agent in the combination therapy that improves the therapeutic index of the combination therapy.

EXAMPLE 44: The method of any one of examples 1-43, further comprising selecting the identity of at least one therapeutic agent in the combination therapy in order to improve the therapeutic index of the combination therapy.

EXAMPLE 45: The method of any one of examples 1-44, further comprising analyzing a biological sample from a patient suspected of suffering from the medical disorder.

EXAMPLE 46: The method of any one of examples 1-44, further comprising selecting the identity of at least one therapeutic agent in the combination therapy based on a feature of a biological sample obtained from a patient suspected of suffering from the medical disorder.

EXAMPLE 47: The method of example 46, wherein the feature is a cancer mutation.

EXAMPLE 48: The method of any one of examples 45-47, wherein the biological sample is a biopsy of a tumor.

EXAMPLE 49: The method of any one of examples 1-48, further comprising evaluating the oxidation state of a biological pathway impacting the medical disorder.

EXAMPLE 50: The method of any one of examples 1-49, further comprising selecting the identity of at least one therapeutic agent in the combination therapy to impact the oxidation state of a biological pathway impacting the medical disorder.

EXAMPLE 51: The method of any one of examples 1-50, further comprising (i) selecting a dosage amount for at least one therapeutic agent in the combination that improves the therapeutic benefit towards the medical disorder or (ii) altering the identity of at least one therapeutic agent in the combination therapy to improve the therapeutic benefit towards the medical disorder.

EXAMPLE 52: The method of any one of examples 1-51, wherein a greater improvement in efficacy towards the medical disorder between (i) the combination and (ii) the most efficacious single therapeutic agent in the combination indicates greater therapeutic benefit.

EXAMPLE 53: The method of any one of examples 1-52, wherein a greater improvement in potency towards the medical disorder for the first therapeutic agent between when (i) the first therapeutic agent is used alone and (ii) the first therapeutic agent is used in combination with the second therapeutic agent indicates greater therapeutic benefit.

EXAMPLE 54: The method of any one of examples 1-53, wherein a greater improvement in potency towards the medical disorder for the second therapeutic agent between when (i) the second therapeutic agent is used alone and (ii) the second therapeutic agent is used in combination with the first therapeutic agent indicates greater therapeutic benefit.

EXAMPLE 55: The method of any one of examples 1-54, wherein the medical disorder is cancer.

EXAMPLE 56: The method of any one of examples 1-55, wherein the combination therapy contains only two therapeutic agents that provide a therapeutic effect against the medical disorder.

What is claimed is:

1. A method for evaluating the therapeutic benefit of a combination therapy comprising a first therapeutic agent and a second therapeutic agent to be used in combination to treat a medical disorder, the method comprising the steps of:
   (a) determining, with an electronic processor, a difference in efficacy towards the medical disorder between (i) the combination and (ii) the most efficacious single therapeutic agent in the combination;
   (b) determining, with the electronic processor, a difference in potency towards the medical disorder for the first therapeutic agent between when (i) the first therapeutic agent is used alone and (ii) the first therapeutic agent is used in combination with the second therapeutic agent;
   (c) determining, with the electronic processor, a difference in potency towards the medical disorder for the second therapeutic agent between when (i) the second therapeutic agent is used alone and (ii) the second therapeutic agent is used in combination with the first therapeutic agent;
   (d) selecting the combination, the first therapeutic agent, or the second therapeutic agent, to prescribe for a patient, based on the determining steps of (a), (b), and (c); and
   optionally, administering the selected one of the combination, the first therapeutic agent, or the second therapeutic agent to the patient.

2. The method of claim 1, wherein step (a) comprises determining, with the electronic processor, for a plurality of different doses for each therapeutic agent in the combination, the difference in efficacy towards the medical disorder between (i) the combination and (ii) the most efficacious single therapeutic agent in the combination.

3. The method of claim 1, wherein step (a) comprises determining, with the electronic processor, across a dosage range for each therapeutic agent in the combination, the difference in efficacy towards the medical disorder between (i) the combination and (ii) the most efficacious single therapeutic agent in the combination.

4. The method of claim 1, wherein step (b) comprises determining, with the electronic processor, for a plurality of different doses of the first therapeutic agent, the difference in potency towards the medical disorder for the first therapeutic agent between when (i) the first therapeutic agent is used alone and (ii) the first therapeutic agent is used in combination with the second therapeutic agent.

5. The method of claim 1, wherein step (c) comprises determining, with the electronic processor, for a plurality of different doses of the second therapeutic agent, the difference in potency towards the medical disorder for the second therapeutic agent between when (i) the second therapeutic agent is used alone and (ii) the second therapeutic agent is used in combination with the first therapeutic agent.

6. The method of claim 1, wherein results from determining, with the electronic processor, the difference in efficacy towards the medical disorder from step (a) are cross-referenced with results from one or both of:
   (i) results from determining the difference in potency towards the medical disorder for the first therapeutic agent from step (b), and
   (ii) results from determining the difference in potency for the second therapeutic agent from step (c);
   to generate a graphical display of therapeutic effect according to the dose of first therapeutic agent and dose of second therapeutic agent.

7. The method of claim 1, wherein the method comprises determining, with the electronic processor, a therapeutic effect (Ed) towards the medical disorder for the combination therapy, at a given concentration of first therapeutic agent and second therapeutic agent, using Equation 1:

$$E_d = \frac{C_1^{h_1} C_2^{h_2} E_0 + d_1^{h_1} C_2^{h_2} E_1 + C_1^{h_1} d_2^{h_2} E_2 + (\alpha_2 d_1)^{h_1} d_2^{h_2} E_3}{C_1^{h_1} C_2^{h_2} + d_1^{h_1} C_2^{h_2} + C_1^{h_1} d_2^{h_2} + (\alpha_2 d_1)^{h_1} d_2^{h_2}}$$ (Equation 1)

wherein:

$C_1$ is the concentration of the first therapeutic agent required to achieve 50% of the maximum efficacy of the combination therapy towards the medical disorder;

$C_2$ is the concentration of the second therapeutic agent required to achieve 50% of the maximum efficacy of the combination therapy towards the medical disorder;

$h_1$ is the Hill coefficient for the dose-response curve of the first therapeutic agent when the first therapeutic agent is used alone;

$h_2$ is the Hill coefficient for the dose-response curve of the second therapeutic agent when the second therapeutic agent is used alone;

$d_1$ is concentration of the first therapeutic agent;

$d_2$ is concentration of the second therapeutic agent;

$E_0$ is the basal effect (i.e. the efficacy when neither the first nor second therapeutic agent is used to treat the medical disorder);

$E_1$ is the maximum efficacy towards the medical disorder of the first therapeutic agent when the first therapeutic agent is used alone;

$E_2$ is the maximum efficacy towards the medical disorder of the second therapeutic agent when the second therapeutic agent is used alone;

$E_3$ is the maximum efficacy towards the medical disorder of the combination therapy; and $\alpha_2$ is the fold-change in the concentration of the first therapeutic agent required to achieve 50% of the maximum efficacy towards the medical disorder of the combination therapy compared to when the first therapeutic agent is used alone.

8. The method of claim 7, wherein the therapeutic effect ($E_d$) is determined, with the electronic processor, at a plurality of different doses for the first therapeutic agent and at a plurality of different doses for the second therapeutic agent.

9. The method of claim 7, wherein determining, with the electronic processor, the therapeutic effect ($E_d$) includes using a Bayesian curve fitting algorithm with a particle swarm optimizer to seed priors for a Markov chain Monte Carlo Optimization.

10. The method of claim 7, wherein the therapeutic effect ($E_d$) is displayed graphically, with the electronic processor, according to the determined therapeutic effect ($E_d$) across different doses for the first therapeutic agent and across different doses for the second therapeutic agent.

11. The method of claim 1, wherein the method comprises determining, with the electronic processor, a therapeutic effect ($E_d$) towards the medical disorder for the combination therapy, at a given concentration of first therapeutic agent and second therapeutic agent, using Equation 2:

$C_2$ is the concentration of the second therapeutic agent required to achieve 50% of the maximum efficacy of the combination therapy towards the medical disorder;

$h_1$ is the Hill coefficient for the dose-response curve of the first therapeutic agent when the first therapeutic agent is used alone;

$h_2$ is the Hill coefficient for the dose-response curve of the second therapeutic agent when the second therapeutic agent is used alone;

$d_1$ is concentration of the first therapeutic agent;

$d_2$ is concentration of the second therapeutic agent;

$E_0$ is the basal effect (i.e. the efficacy when neither the first nor second therapeutic agent is used to treat the medical disorder);

$E_1$ is the maximum efficacy towards the medical disorder of the first therapeutic agent when the first therapeutic agent is used alone;

$E_2$ is the maximum efficacy towards the medical disorder of the second therapeutic agent when the second therapeutic agent is used alone;

$E_3$ is the maximum efficacy towards the medical disorder of the combination therapy;

$\alpha_1$ is the fold-change in the concentration of the second therapeutic agent required to achieve 50% of the maximum efficacy towards the medical disorder of the combination therapy compared to when the second therapeutic agent is used alone;

$\alpha_2$ is the fold-change in the concentration of the first therapeutic agent required to achieve 50% of the maximum efficacy towards the medical disorder of the combination therapy compared to when the first therapeutic agent is used alone;

$r_1$ is the rate of transition for the first therapeutic agent from the unaffected state to the affected state;

$r_{-1}$ is $r_1 * C_1^{h_1}$;

$r_2$ is the rate of transition for the second therapeutic agent from the unaffected state to the affected state; and $r_{-2}$ is $r_2 * C_2^{h_2}$.

12. The method of claim 11, wherein the therapeutic effect ($E_d$) is determined, with the electronic processor, at a plurality of different doses for the first therapeutic agent and at a plurality of different doses for the second therapeutic agent.

13. The method of claim 11, wherein determining, with the electronic processor, the therapeutic effect (Ed) includes using a Bayesian curve fitting algorithm with a particle swarm optimizer to seed priors for a Markov chain Monte Carlo Optimization.

14. The method of claim 11, wherein the therapeutic effect ($E_d$) is displayed graphically, with the electronic processor, according to the determined therapeutic effect ($E_d$) across different doses for the first therapeutic agent and different doses for the second therapeutic agent.

$$E_d = [E_0 E_1 E_2 E_3] \cdot \begin{bmatrix} -(r_1 d_1^{h_1} + r_2 d_2^{h_2}) & r_{-1} & r_{-2} & 0 \\ r_1 d_1^{h_1} & -(r_{-1} + r_2(\alpha_1 d_2)^{h_2}) & 0 & r_{-2} \\ r_2 d_2^{h_2} & 0 & -(r_1(\alpha_2 d_1)^{h_1} + r_{-2}) & r_{-1} \\ 1 & 1 & 1 & 1 \end{bmatrix}^{-1} \cdot \begin{bmatrix} 0 \\ 0 \\ 0 \\ 1 \end{bmatrix}$$

(Equation 2)

wherein:

$C_1$ is the concentration of the first therapeutic agent required to achieve 50% of the maximum efficacy of the combination therapy towards the medical disorder;

15. The method of claim 1, further comprising evaluating, with the electronic processor, the pharmacokinetic properties of all therapeutic agents in the combination therapy; and selecting, with the electronic processor, at least one selected from a group consisting of a dosage amount and an identity of at least one therapeutic agent in the combination therapy to improve the therapeutic benefit of the combination in view of the pharmacokinetic properties.

16. The method of claim 1, further comprising evaluating, with the electronic processor, the safety profile of all therapeutic agents in the combination therapy; and selecting, with the electronic processor, at least one selected from a group consisting of a dosage amount and an identity for at least one therapeutic agent in the combination therapy that improves the safety profile of the combination therapy.

17. The method of claim 1, further comprising evaluating, with the electronic processor, a toxicity profile of all therapeutic agents in the combination therapy, and selecting, with the electronic processor, at least one selected from a group consisting of a dosage amount and an identity for at least one therapeutic agent in the combination therapy that improves the toxicity profile of the combination therapy.

18. The method of claim 1, further comprising evaluating, with the electronic processor, patient biological pathways of all therapeutic agents in the combination therapy; and selecting, with the electronic processor, the identity of at least one therapeutic agent in the combination therapy so that the combination therapy impacts at least two different biological pathways in the patient in order to improve the therapeutic benefit of the combination.

19. The method of claim 1, further comprising evaluating, with the electronic processor, the therapeutic index of all therapeutic agents in the combination therapy; and selecting, with the electronic processor, at least one selected from a group consisting of a dosage amount and an identity of at least one therapeutic agent in the combination therapy that improves the therapeutic index of the combination therapy.

20. The method of claim 1, further comprising (i) selecting, with the electronic processor, a dosage amount for at least one therapeutic agent in the combination that improves the therapeutic benefit towards the medical disorder or (ii) altering, with the electronic processor, the identity of at least one therapeutic agent in the combination therapy to improve the therapeutic benefit towards the medical disorder.

* * * * *